(12) United States Patent
Delaney et al.

(10) Patent No.: US 12,097,238 B2
(45) Date of Patent: Sep. 24, 2024

(54) AQUEOUS SOLUTION COMPRISING A GLUTATHIONE SALT

(71) Applicant: RENOVION, INC., Chapel Hill, NC (US)

(72) Inventors: Edward J. Delaney, Princeton, NJ (US); Carolyn Durham, Chapel Hill, NC (US); Daniel W. Copeland, Chapel Hill, NC (US)

(73) Assignee: Renovion, Inc., Chapel Hill, NC (US)

( * ) Notice: Subject to any disclaimer, the term of this patent is extended or adjusted under 35 U.S.C. 154(b) by 0 days.

(21) Appl. No.: 18/640,964

(22) Filed: Apr. 19, 2024

(65) Prior Publication Data

US 2024/0285722 A1    Aug. 29, 2024

Related U.S. Application Data

(63) Continuation of application No. PCT/US2023/010081, filed on Jan. 4, 2023.

(60) Provisional application No. 63/296,405, filed on Jan. 4, 2022.

(51) Int. Cl.
  *A61K 38/06* (2006.01)
  *A61K 9/08* (2006.01)
  *A61K 31/375* (2006.01)

(52) U.S. Cl.
  CPC ............. *A61K 38/063* (2013.01); *A61K 9/08* (2013.01); *A61K 31/375* (2013.01)

(58) Field of Classification Search
  None
  See application file for complete search history.

(56) References Cited

U.S. PATENT DOCUMENTS

| | | | |
|---|---|---|---|
| 2,606,903 A | 8/1952 | Ruskin | |
| 4,861,783 A | 8/1989 | Ackerman et al. | |
| 4,968,716 A | 11/1990 | Markham | |
| 5,070,085 A | 12/1991 | Markham | |
| 5,238,683 A | 8/1993 | Crystal | |
| 5,304,724 A | 4/1994 | Newton | |
| 5,626,883 A | 5/1997 | Paul | |
| 5,824,693 A | 10/1998 | Goldberg | |
| 5,829,449 A | 11/1998 | Hersh et al. | |
| 5,989,521 A | 11/1999 | Crystal | |
| 6,159,500 A | 12/2000 | Demopoulos et al. | |
| 6,228,347 B1 | 5/2001 | Hersh | |
| 6,312,734 B1 | 11/2001 | Kozhemyakin et al. | |
| 6,350,467 B1 | 2/2002 | Demopoulos et al. | |
| 6,423,687 B1 | 7/2002 | Demopoulos et al. | |
| 6,601,580 B1 | 8/2003 | Bloch | |
| 6,723,703 B2 | 4/2004 | Gaston et al. | |
| 6,764,693 B1 | 7/2004 | Smith | |
| 7,026,342 B2 | 4/2006 | Wagle et al. | |
| 7,384,976 B2 | 6/2008 | Garvey | |
| 9,308,234 B2 | 4/2016 | Arnold et al. | |
| 10,328,152 B2 | 6/2019 | Patel et al. | |
| 10,406,200 B2 | 9/2019 | Arnold et al. | |
| 11,058,743 B2 | 7/2021 | Arnold et al. | |
| 11,344,529 B2 | 5/2022 | Van Wyk et al. | |
| 11,497,786 B2 | 11/2022 | Copeland et al. | |
| 11,602,555 B2 | 3/2023 | Copeland et al. | |
| 11,890,315 B2 | 2/2024 | Copeland et al. | |
| 2002/0037855 A1 | 3/2002 | Stanislaus | |
| 2002/0136763 A1 | 9/2002 | Demopoulos et al. | |
| 2002/0165207 A1 | 11/2002 | Rosenbloom | |
| 2002/0179103 A1 | 12/2002 | Hersh et al. | |
| 2003/0064494 A1 | 4/2003 | Kumar et al. | |
| 2003/0119909 A1 | 6/2003 | Stanislaus | |
| 2004/0071770 A1 | 4/2004 | Smith | |
| 2004/0229815 A1 | 11/2004 | Nagasawa et al. | |
| 2006/0018945 A1 | 1/2006 | Britigan et al. | |
| 2006/0204557 A1 | 9/2006 | Gupta et al. | |
| 2006/0228693 A1 | 10/2006 | Soll | |
| 2006/0258599 A1 | 11/2006 | Childers | |
| 2007/0049641 A1 | 3/2007 | Tirouvanziam et al. | |
| 2008/0008694 A1 | 1/2008 | Elgebaly et al. | |
| 2009/0214674 A1 | 8/2009 | Barraud et al. | |
| 2009/0270310 A1 | 10/2009 | Whyte | |
| 2010/0310541 A1 | 12/2010 | Kessler et al. | |
| 2010/0311837 A1 | 12/2010 | Sakai et al. | |
| 2012/0021071 A1 | 1/2012 | Bordeau et al. | |
| 2012/0093947 A1 | 4/2012 | Britigan et al. | |

(Continued)

FOREIGN PATENT DOCUMENTS

| | | |
|---|---|---|
| AU | 2004315267 A1 | 8/2005 |
| AU | 2004315267 B2 | 1/2009 |
| AU | 2005305456 B2 | 5/2011 |
| CA | 2058793 A1 | 7/1992 |
| CA | 2339473 A1 | 2/2000 |
| CA | 2620123 A1 | 3/2007 |
| CA | 2620123 C | 11/2011 |
| CN | 1921876 A | 2/2007 |
| CN | 101175499 B | 12/2010 |
| CN | 101987195 A | 3/2011 |
| CN | 102100904 B | 4/2013 |
| CN | 102329370 B | 7/2015 |

(Continued)

OTHER PUBLICATIONS

Avgeri, S.G., et al., "Therapeutic Options for Burkholderia Cepacia Infections Beyond Co-trimoxazole: a Systematic Review of the Clinical Evidence," International Journal of Antimicrobial Agents 33(5):394-404, Elsevier Science Publishers, Netherlands (May 2009).

(Continued)

*Primary Examiner* — Christina Bradley
(74) *Attorney, Agent, or Firm* — Sterne, Kessler, Goldstein & Fox P.L.L.C.

(57) ABSTRACT

This disclosure provides pharmaceutical preparations, products, and methods relating to ARINA-1 for use in treating patients with chronic inflammatory lung diseases, such as lung transplant, cystic fibrosis (CF), non-CF bronchiectasis, chronic obstructive pulmonary disease (COPD, and other inflammatory lung diseases.

17 Claims, 5 Drawing Sheets

(56) References Cited

U.S. PATENT DOCUMENTS

| | | | |
|---|---|---|---|
| 2013/0084336 | A1 | 4/2013 | Friedman et al. |
| 2013/0129815 | A1 | 5/2013 | Guilford et al. |
| 2015/0010654 | A1 | 1/2015 | Arnold et al. |
| 2015/0374626 | A1 | 12/2015 | Guilford |
| 2016/0367620 | A1 | 12/2016 | Demopoulos |
| 2016/0367621 | A1 | 12/2016 | Demopoulos et al. |
| 2019/0231686 | A1 | 8/2019 | Burch |
| 2019/0351005 | A1* | 11/2019 | Copeland ............... A61K 9/007 |
| 2020/0179478 | A1 | 6/2020 | Arnold et al. |
| 2020/0361973 | A1 | 11/2020 | Liu et al. |
| 2020/0397849 | A1 | 12/2020 | Copeland et al. |
| 2022/0000966 | A1 | 1/2022 | Hoag et al. |
| 2022/0143129 | A1 | 5/2022 | Arnold et al. |
| 2023/0165929 | A1 | 6/2023 | Copeland et al. |

FOREIGN PATENT DOCUMENTS

| | | |
|---|---|---|
| DE | 19935763 A1 | 2/2001 |
| DE | 102004035113 A1 | 2/2006 |
| EP | 0938331 B1 | 12/2002 |
| EP | 1282416 A2 | 2/2003 |
| EP | 1701732 A2 | 9/2006 |
| EP | 1474158 B1 | 10/2009 |
| EP | 1333823 B1 | 3/2010 |
| JP | 2004514650 A | 5/2004 |
| JP | 4652664 B2 | 3/2011 |
| WO | WO-9819694 A1 | 5/1998 |
| WO | WO-99000106 A1 | 1/1999 |
| WO | WO-2001002004 A1 | 1/2001 |
| WO | WO-01089520 A2 | 11/2001 |
| WO | WO-01089520 A3 | 11/2001 |
| WO | WO-0232418 A1 | 4/2002 |
| WO | WO-2002091866 A1 | 11/2002 |
| WO | WO-2005074903 A2 | 8/2005 |
| WO | WO-2005074903 A3 | 8/2005 |
| WO | WO-2005120457 A1 | 12/2005 |
| WO | WO-2006054304 A2 | 5/2006 |
| WO | WO-2006060120 A2 | 6/2006 |
| WO | WO-2006060120 A3 | 6/2006 |
| WO | WO-2007024876 A2 | 3/2007 |
| WO | WO-2007024876 A3 | 3/2007 |
| WO | WO-2007134180 A2 | 11/2007 |
| WO | WO-2009001884 A1 | 12/2008 |
| WO | WO-2009069291 A1 | 6/2009 |
| WO | WO-2010033292 A2 | 3/2010 |
| WO | WO-2010086530 A1 | 8/2010 |
| WO | WO-2010131038 A2 | 11/2010 |
| WO | WO-2012017367 A1 | 2/2012 |
| WO | WO-2012027603 A2 | 3/2012 |
| WO | WO-2012085582 A1 | 6/2012 |
| WO | WO-2014070769 A1 | 5/2014 |
| WO | WO-2014127245 A1 | 8/2014 |
| WO | WO-2014132123 A2 | 9/2014 |
| WO | WO-2016037166 A1 | 3/2016 |
| WO | WO-2016067283 A1 | 5/2016 |
| WO | WO-2016088116 A1 | 6/2016 |
| WO | WO-2018094278 A1 | 5/2018 |
| WO | WO-2019099946 A1 | 5/2019 |
| WO | WO-2020211653 A1 | 10/2020 |
| WO | WO-2024016019 A1 | 1/2024 |

OTHER PUBLICATIONS

Bishop, C., et al., "A Pilot Study of the Effect of Inhaled Buffered Reduced Glutathione on the Clinical Status of Patients with Cystic Fibrosis," Chest Journal 127 (1):308-317, Elsevier, Netherlands (Jan. 2005).

Bjarnsholt, T., "The role of bacterial biofilms in chronic infections," 136:1-51, APMIS Suppl., Blackwell Publishing Ltd., United States (May 2013).

Boies, et al., "Fundamentals of Otolaryngology," W. B. Saunders Co., Philadelphia, 1989, pp. 184.

Boyanova, et al., "Coadministration of probiotics with antibiotics: why, when and for how long?," Expert Rev Anti Infect Ther 10(4):407-409, Taylor & Francis, United States (2014).

Bray, T.M., and Taylor, C.G., "Tissue Glutathione, Nutrition, and Oxidative Stress," Canadian Journal of Physiology and Pharmacology 71(9):746-751, Canadian Science Publishing, Canada (Sep. 1993).

Cursino, L., et al., "Synergic interaction between ascorbic acid and antibiotics against Pseudomonas aeruginosa," Brazilian Archives of Biology and Technology 48(3): 379-384, Brazilian Archives of Biology and Technology, Brazil (2005).

Donnelly, L.E., et al., "Defective Phagocytosis in Airways Disease," Chest 141(4):1055-1062, Elsevier, Netherlands (Apr. 2012).

Fitzpatrick, A.M., et al., "Glutathione oxidation is associated with airway macrophage functional impairment in children with severe asthma," Pediatric Res 69(2):154-159, International Pediatric Research Foundation Inc., United States (Feb. 2011).

International Search Report and Written Opinion for Application No. PCT/US2018/061686, mailed on Jan. 25, 2019, 8 pages.

Klockgether, J., et al., "Genome Diversity of Pseudomonas Aeruginosa PAO1 Laboratory Strains," Journal of Bacteriology, 192(4):1113-1121, American Society for Microbiology, United States (Feb. 2010).

Sánchez, C. et al., "Inter-Subject Variability in Human Atrial Action Potential in Sinus Rhythm versus Chronic Atrial Fibrillation," PLOS One 9(8):e105897, Public Library of Science, United States (Aug. 2014).

Sass, A.M., et al., "The Unexpected Discovery of a Novel Low-oxygen-activated Locus for the Anoxic Persistence of Burkholderia Cenocepacia," The ISME Journal 7(8):1568-1581, Nature Publishing Group, England (Aug. 2013).

Schwab, U., et al., "Localization of Burkholderia Cepacia Complex Bacteria in Cystic Fibrosis Lungs and Interactions With *Pseudomonas aeruginosa* in Hypoxic Mucus," Infection and immunity 82(11):4729-4745, American Society for Microbiology, United States (Nov. 2014).

Shields, R.K., et al., "*Staphylococcus aureus* Infections in the Early Period After Lung Transplantation: Epidemiology, Risk Factors, and Outcomes," The Journal of Heart and Lung Transplantation 31(11):1199-1206, Elsevier, United States (Nov. 2012).

Simpson, G.LW., and Ortwerth, B.J., "The Non-Oxidative Degradation of Ascorbic Acid at Physiological Conditions," Biochimica et Biophysica Acta, 1501(1):12-24, Elsevier Pub. Co, Netherlands (Apr. 2000).

Taglietti, A., et al., "Antibacterial Activity of Glutathione-Coated Silver Nanoparticles against Gram Positive and Gram Negative Bacteria," Langmuir, 28(21):8140-8148, American Chemical Society, United States (May 2012).

Tong, S.Y.C., et al., "*Staphylococcus aureus* Infections: Epidemiology, Pathophysiology, Clinical Manifestations, and Management," Clinical Microbiology Reviews 28(3):603-661, American Society for Microbiology, United States (Jul. 2015).

Varga, J.J., et al., "Genotypic and Phenotypic Analyses of a Pseudomonas Aeruginosa Chronic Bronchiectasis Isolate Reveal Differences From Cystic Fibrosis and Laboratory Strains, " BMC Genomics 16:883, BioMed Central, England (Oct. 2015).

Visca, A., et al., "Improvement in clinical markers in CF patients using a reduced glutathione regimen: an uncontrolled, observational study," Journal of Cystic Fibrosis 7:433-436, Elsevier, Netherlands (Sep. 2008).

Wagner, T., et al., "Effects of Azithromycin on Clinical Isolates of Pseudomonas Aeruginosa From Cystic Fibrosis Patients," Chest 128(2):912-919, Elsevier Ltd., United States (Aug. 2005).

Zhang, Y and Duan, K., "Glutathione Exhibits Antibacterial Activity and Increases Tetracycline Efficacy against Pseudomonas Aeruginosa," Science China Life Sciences, 52(6):501-505, Science in China Press, co published with Springer-Verlag, China (Jun. 2009).

Zhao, J., et al., "Decade-long Bacterial Community Dynamics in Cystic Fibrosis Airways," Proceedings of the National Academy of Sciences of the United States of America 109(15):5809-5814, National Academy of Sciences, United States (Apr. 2012).

(56) References Cited

OTHER PUBLICATIONS

Atkuri et al., "N-Acetylcysteine-a safe antidote for cysteine/glutathione deficiency" Current Opinion in Pharmacology 7(4):355-359, Elsevier BV, Netherlands (Aug. 2007).
Bergamini et al., "Azithromycin Decreases Glutathione-S-Transferase T1 (GSTT1) and M1 (GSTM1) Expression and Activity in Cystic Fibrosis Airway Epithelial Cells" Pediatric Pulmonology 42(Suppl. 30):297 Abstract 269 (2007) (1 page).
Bergamini et al., "Effects of Azithromycin on Glutathione S-Transferases in Cystic Fibrosis Airway Cells" American Journal of Respiratory Cell and Molecular Biology 41(2):199-206 (Aug. 2009).
Brechbuhl et al., "Glutathione transport is a unique function of the ATP-binding cassette protein ABCG2" Journal of Biological Chemistry 285(22):16582-16587 (May 2010).
Cantin, A.M., "Potential for antioxidant therapy of cystic fibrosis" Current Opinion in Pulmonary Medicine 10(6):531-536, Lippincott Williams and Wilkins Ltd., United States (Nov. 2004).
Caraher, E.M., et al., "The effect of recombinant human lactoferrin on growth and the antibiotic susceptibility of the cystic fibrosis pathogen Burkholderia cepacia complex when cultured planktonically or as biofilms" Journal of Antimicrobial Chemotherapy 60:546-554, Oxford University Press, United Kingdom (Sep. 2007).
Carter, C.J., "Pathogen and autoantigen homologous regions within the cystic fibrosis transmembrane conductance regulator (CFTR) protein suggest an autoimmune treatable component of cystic fibrosis" FEMS Immunology and Medical Microbiology 62(2):197-214, Elsevier, Netherlands (Jul. 2011).
Cheluvappa et al., "Reactions of Pseudomonas aeruginosa pyocyanin with reduced glutathione," Acta Biochimica Polonica 55(3):571-580, Frontiers Media SA, Poland (2008).
Cheng, S., et al., "The PDZ domain protein CAL interacts with mGluR5a and modulates receptor expression" Journal of Neurochemistry 112(3):588-598, Wiley-Blackwell Publishing Ltd., United Kingdom (Feb. 2010).
Childers, M., et al., "A new model of cystic fibrosis pathology: Lack of transport of glutathione and its thiocyanate conjugates" Medical Hypotheses 68(1):101-112, Churchill Livingstone, United States (2007).
Ciofu, O., et al., "Respiratory bacterial infections in cystic fibrosis," Current Opinion in Pulmonary Medicine 19(3):251-258, Lippincott Williams and Wilkins Ltd., United States (May 2013).
Clunes, M.T., et al., "Cystic fibrosis: the mechanisms of pathogenesis of an inherited lung disorder," Drug Discovery Today 4(2):63-72, Elsevier Ltd., United Kingdom (2007).
Colombo, J.L., "Long-acting bronchodilators in cystic fibrosis," Curr Opin Pulm Med 9(6):504-508, Lippincott Williams and Wilkins Ltd., United States (Nov. 2003).
Conner, G.E., et al., "The lactoperoxidase system links anion transport to host defense in cystic fibrosis" FEBS Lett 581(2):271-278, Wiley-Blackwell, United States (Jan. 2007).
Dauletbaev, N., et al., "A Phase II Study on Safety and Efficacy of High-Dose N-Acetylcysteine in Patients with Cystic Fibrosis," Eur J Med Res 14(8):352-358, BioMed Central Ltd., United Kingdom (Aug. 2009).
Day, B.J., et al., "Role for Cystic Fibrosis Transmembrane Conductance Regulator Protein in a Glutathione Response to Bronchopulmonary Pseudomonas Infection," Infect Immun 72(4):2045-2051, American Society for Microbiology, United States (Apr. 2004).
Day, Brian J. "Glutathione-A Radical Treatment for Cystic Fibrosis Lung Disease?" Chest 127(1):12-14, American College of Chest Physicians, United States (Jan. 2005).
Donnelly, L.E., et al., "Defective Phagocytosis in Airways Disease," Chest 141(4):1055-1062, American College of Chest Physicians, United States (Apr. 2012).
D'orazio, M., et al., "Extracellular Glutathione Decreases the Ability of Burkholderia cenocepacia to Penetrate into Epithelial Cells and to Induce an Inflammatory Response," PLOS One 7(10):e47550, Public Library of Science, United States (2012).

Elsheikh, A., et al., "Enhanced antigenicity leads to altered immunogenicity in sulfamethoxazole-hypersensitive patients with cystic fibrosis," J Allergy Clin Immunol 127(6):15431551.e3, Mosby Inc., United States (Jun. 2011).
England, R.J., et al., "Nasal pH measurement: a reliable and repeatable parameter," Clin Otolaryngol Allied Sci 24(1):67-68, Wiley, United States (Feb. 1999).
Feuillet-Fieux, M.N., et al., "Glutathione S-transferases Related to P. aeruginosa Lung Infection in Cystic Fibrosis Children: Preliminary Study," Clinical Biochemistry 42(1-2):57-63 Elsevier Inc., United States (Jan. 2009).
Fischer, H., "Mechanisms and Function of DUOX in Epithelia of the Lung, " Antioxid Redox Signal 11(10):2453-2465, Mary Ann Liebert Inc., United States (Oct. 2009).
Fisher, A.J., and PAS, R.H.T., "Clinical evaluation of ascoxal a new mucolytic agent," Anesth Analg 45(5):531-534, Lippincott Williams and Wilkins Ltd., United States (Sep.-Oct. 1966).
Flamant, C., et al., "Glutathione-S-transferase M1 M3, P1 and T1 polymorphisms and severity of lung disease in children with cystic fibrosis," Pharmacogenetics 14(5):295-301, Lippincott Williams and Wilkins Ltd., United States (May 2004).
Gao, L., et al., "Abnormal glutathione transport in cystic fibrosis airway epithelia," Am J Physiol 277(1):L113-L118, American Physiological Society, United States (Jul. 1999).
Gao, L., et al., "Synthetic chloride channel restores glutathione secretion in cystic fibrosis airway epithelia," Am J Physiol Lung Cell Mol Physiol 281(1):L24-L30, American Physiological Society, United States (Jul. 2001).
Geller, D.E., "Aerosol Antibiotics in Cystic Fibrosis," Respir Care 54(5):658-670, Daedalus Enterprises Inc., United States (May 2009).
Gerson, C., et al., "The Lactoperoxidase System Functions in Bacterial Clearance of Airways," Am J Respir Cell Mol Biol 22:665-671, American Thoracic Society, United States (Jun. 2000).
Gould, N., and Day, B.J., "Targeting maladaptive glutathione responses in lung disease," Biochemical Pharmacology 81(2):187-193, Elsevier Inc., United States (Jan. 2011).
Govindaraju, K., et al., "Analysis of Glutathione in Rat Airway Surface Liquid by Capillary Zone Electrophoresis with Conductivity Detection," Journal of Chromatography B-Analytical Technologies in the Biomedical and Life Sciences 788(2):369-376, Elsevier, Netherlands (May 2003).
Griese, M., et al., "Improvement of Alveolar Glutathione and Lung Function but Not Oxidative State in Cystic Fibrosis," Am J Respir Crit Care Med 169(7):822-828, American Thoracic Society, United States (Apr. 2004).
Griese, M., et al., "Inhalation Treatment with Glutathione in Patients with Cystic Fibrosis," Am J Respir Crit Care Med 188(1):83-89, American Thoracic Society, United States (Jul. 2013).
Grigoras, I., et al., "Functional Characterization of the Saccharomyces cerevisiae ABC-transporter Yorlp Overexpressed in Plasma Membranes," Biochim Biophys Acta 1778(1):68-78, Elsevier, Netherlands (Jan. 2008).
Gukasyan, H.J., et al., "Glutathione and its transporters in ocular surface defense," Ocul Surf 5(4):269-279, Elsevier Inc., United States (Oct. 2007).
Hartl D., et al., "Inhaled glutathione decreases PGE2 and increases lymphocytes in cystic fibrosis lungs," Free Radic Biol Med 39(4):463-472, Elsevier Inc., United States (Aug. 2005).
Wood, L.G., et al., "Biomarkers of lipid peroxidation, airway inflammation and asthma," Eur Respir J 21(1):177-186, European Respiratory Society, Switzerland (Jan. 2003).
Hector et al., "Glutathione in Airway Neutrophils in Cystic Fibrosis," Pediatric Pulmonology 44(Suppl. 32) Abstract 420:359-360 (2009).
Hector, A., et al., "Novel Method to Process Cystic Fibrosis Sputum for Determination of Oxidative State," Respiration 80(5):393-400 S. Karger AG, Switzerland (2010).
Henrion-Caude, A., et al., "Liver disease in pediatric patients with cystic fibrosis is associated with glutathione S-transferase P1 polymorphism," Hepatology 36(4):913-917, John Wiley and Sons Ltd., United States (Oct. 2002).

(56) References Cited

OTHER PUBLICATIONS

Howell, L.D., et al., "ATP hydrolysis by a CFTR domain: Pharmacology and effects of G551D mutation," Biochem Biophys Res Commun 271(2):518-525, Academic Press Inc., United States (May 2000).
Huang, Y.J., et al., "Airway Microbiota and Bronchial Hyperresponsiveness in Patients with Suboptimally Controlled Asthma," J Allergy Clin Immunol 127(2):372-381.e3, Mosby Inc., United States (Feb. 2011).
Hudson, V.M., Valerie "Differing Compartments of Intracellular Glutathione Have Differing Levels of Glutathione in Cystic Fibrosis," Med Hypotheses 68(4):919-920, Churchill Livingstone, United States (2007).
Hudson, V.M., "Rethinking cystic fibrosis pathology: The critical role of abnormal reduced glutathione (GSH) transport caused by CFTR mutation," Free Radic Biol Med 30(12):1440-1461, Elsevier Inc., United States (Jun. 2001).
Inci, I., et al., "Prevention of primary graft dysfunction in lung transplantation by N-acetylcysteine after prolonged cold ischemia," J Heart Lung Transplant 29(11):1293-1301, Elseveir USA, United States (Nov. 2010).
Innis, S.M., et al., "Choline-related supplements improve abnormal plasma methionine-homocysteine metabolites and glutathione status in children with cystic fibrosis," Am J Clin Nutr 85(3):702-708, American Society for Nutrition, United States (Mar. 2007).
Lehr "Global Markets for Asthma and COPD Drugs," BCC Research Market Forecasting 1-159 (2012).
Nagavarapu "Pulmonary Drug Delivery Systems: Technologies and Global Markets," BCC Research Market Forecasting:1-222 (2012).
Jungas, T., et al., "Glutathione levels and BAX activation during apoptosis due to oxidative stress in cells expressing wild-type and mutant cystic fibrosis transmembrane conductance regulator," J Biol Chem 277(31):27912-27918, Elsevier Inc., United States (Aug. 2002).
Kariya, C., et al., "A role for CFTR in the elevation of glutathione levels in the lung by oral glutathione administration," Am J Physiol Lung Cell Mol Physiol 292(6):L1590-L1597, American Physiological Society, United States (Jun. 2007).
Kogan, I., et al., "CFTR directly mediates nucleotide-regulated glutathione flux," Embo J 22(9):1981-1989, Wiley-Blackwell, Germany (May 2003).
Korytina, G.F., et al., "Polymorphism of glutathione S-transferase M1 and P1 in patients with cystic fibrosis and chronic respiratory diseases," Russian Journal of Genetics 40(3):314-320 (Mar. 2004).
Lands, L.C., et al., "Lymphocyte Glutathione Levels in Children with Cystic Fibrosis," Chest 116:201-205, American College of Chest Physicians, United States (Jul. 1999).
Lands, L.C., et al., "Total Plasma Antioxidant Capacity in Cystic Fibrosis," Pediatric Pulmonology 29(2):81-87, Wiley-Liss Inc., United States (Feb. 2000).
Lands, L.C. "Nutrition in pediatric lung disease," Paediatric Respir Rev 8(4):305-312 (Dec. 2007).
Laskowska-Klita, T., et al., "Antioxidant status in erythrocytes of cystic fibrosis children," Acta Biochimica Polonica 48(1):283-285, Acta Biochimica Polonica, Poland (2001).
Lasry, A., et al., "Inflammatory networks underlying colorectal cancer," Nat Immunol, 17(3)230-240, Nature Publishing Group, United Kingdom (Mar. 2016).
Li, C., et al., "Spatiotemporal Coupling of CAMP Transporter to CFTR Chloride Channel Function in the Gut Epithelia," Cell 131(5):940-951, Cell Press, United States (Nov. 2007).
Lima, C., et al., "Cystic fibrosis transmembrane conductance regulator gene mutations and glutathione S-transferase null genotypes in cystic fibrosis patients in Brazil," J Bras Pneumol 38(1):50-56, Sociedade Brasileira de Pneumologia e Tisiologia, Brazil (Jan.-Feb. 2012).
Lothian, J.B., et al., "Effect of whey protein to modulate immune response in children with atopic asthma," Int J Food Sci Nutr 57(3-4):204-211, Informa Healthcare, United Kingdom (May-Jun. 2006).

Madarasi, A., et al., "Antioxidant Status in Patients with Cystic Fibrosis," Ann Nutr Metab 44(5-6):207-211, S. Karger AG, Switzerland (2000).
Martin, C., et al., "Host-microbe interactions in distal airways: relevance to chronic airway diseases," Eur Respir Rev 24(135):78-91, European Respiratory Society, Switzerland (Mar. 2015).
Mckone, E.F., et al., "Variants in the Glutamate-Cysteine-Ligase Gene Are Associated with Cystic Fibrosis Lung Disease," Am J Respir Crit Care Med 174(4):415-419, American Thoracic Society, United States (Aug. 2006).
Moskwa, P., et al., "A Novel Host Defense System of Airways is Defective in Cystic Fibrosis," Am J Respir Crit Care Med 175(2):174-183, American Thoracic Society, United States (Jan. 2007).
Murphy, T.F. "The role of bacteria in airway inflammation in exacerbations of chronic obstructive pulmonary disease," Curr Opin Infect Dis 19(3):225-230, Lippincott Williams and Wilkins Ltd., United States (Jun. 2006).
None, L.V., et al., "Residual Gravimetric Method to Measure Nebulizer Output," J Aerosol Med 17(1):63-72, Mary Ann Liebert, United States (2004).
O'brien, P.J., "Peroxidases," Chem Biol Interact 129(1-2):113-139, Elsevier Ireland Ltd., Ireland (Dec. 2000).
Perez-Vilar, J., and Boucher, R.C., "Reevaluating Gel-Forming Mucins' Roles in Cystic Fibrosis Lung Disease," Free Radic Biol Med 37(10):1564-1577, Elsevier Inc., United States (Nov. 2004).
Pitt, B.R. "CFTR trafficking and signaling in respiratory epithelium," Am J Physiol Lung Cell Mol Physiol 281(1):L13-L15, American Physiological Society, United States (Jul. 2001).
Prousky, J., "The Treatment of Pulmonary Diseases and Respiratory-Related Conditions with inhaled (Nebulized or Aerosolized) Glutathione," Evid Based Complement Alternat Med 5(1):27-35, Hindawi Publishing Corporation, United States (Mar. 2008).
Rada, B., "The Pseudomonas Toxin Pyocyanin Inhibits the Dual Oxidase-Based Antimicrobial System as It Imposes Oxidative Stress on Airway Epithelial Cells," J Immunol 181(7):4883-4893, American Association of Immunologists, United States (Oct. 2008).
Remund, K.F., et al., "Infections Relevant to Lung Transplantation," Proc Am Thorac Soc 6(1):94-100 (Jan. 2009).
Rogan, M.P., et al., "Loss of Microbicidal Activity and increased Formation of Biofilm Due to Decreased Lactoferrin Activity in Patients with Cystic Fibrosis," J Infect Dis 190(7):1245-1253, Oxford University Press, United Kingdom (Oct. 2004).
Roux et al., "Mycobacterium abscessus, pathogène émergent dans la mucoviscidose," Immuno-analyse et biologie specialisee 25(1):26-33 (2010) English Abstract Only.
Schwarzer, C., et al., "Organelle redox of CF and CFTR-corrected airway epithelia," Free Radic Biol Med 43(2):300-316, Elsevier Inc., United States (Jul. 2007).
Schwarzer, C., et al., "Oxidative Stress Caused by Pyocyanin Impairs CFTR Cl-Transport in Human Bronchial Epithelial Cells," Free Radic Biol Med 45(12):1653-1662, Elsevier Inc., United States (Dec. 2008).
Šidlová, K., et al., "Serum alpha-glutathione S-transferase as a sensitive marker of hepatocellular damage in patients with cystic fibrosis," Physiol Res 52(3):361-365,Czech Academy of Sciences, Czech Republic (2003).
Snyder, A.H., et al., "Acute effects of aerosolized S-nitrosoglutathione in cystic fibrosis," Am J Respir Crit Care Med 165(7):922-926, American Thoracic Society, United States (Apr. 2002).
Sonni, F., et al., "Antioxidant Action of Glutathione and the Ascorbic Acid/Glutathione Pair in a Model White Wine," J Agric Food Chem 59(8):3940-3949, American Chemical Society, United States (Apr. 2011).
Speich, R., and Van Der Bij, W., "Epidemiology and Management of Infections after Lung Transplantation," Clin Infect Dis 33(Suppl 1):S58-S65, Oxford University Press, United Kingdom (Jul. 2001).
Szentpétery, Z., et al., "Functional Studies on the MRP1 Multidrug Transporter: Characterization of ABC-Signature Mutant Variants," Anticancer Res 24(2A):449-455, International Institute of Anticancer Research, Greece (Mar.-Apr. 2004).
Thomas, E.L., and Aune, T.M., et al., "Lactoperoxidase, peroxide, thiocyanate antimicrobial system: correlation of sulfhydryl oxida-

(56) References Cited

OTHER PUBLICATIONS tion with antimicrobial action," Infect Immun 20(2):456-483, American Society for Microbiology, United States (May 1978).
Thome, U., et al., "Novel SIN-1 Reactive Intermediates Modulate Chloride Secretion Across Murine Airway Cells," Free Radic Biol Med 35(6):662-675, Elsevier Inc., United States (Sep. 2003).
Tirouvanziam, R., et al., "High-dose oral N-acetylcysteine, a glutathione prodrug, modulates inflammation in cystic fibrosis," Proc Natl Acad Sci USA 103(12):4628-4633, National Academy of Sciences, United States (Mar. 2006).
Tournoud, M., et al., "Structural equations to model relationships between pulmonary function, fatty acids and oxidation in cystic fibrosis," Scand J Clin Lab Invest 69(1):36-44, Informa Healthcare, United Kingdom (2009).
Vasu, V.T., et al., "Evaluation of thiol-based antioxidant therapeutics in cystic fibrosis sputum: Focus on myeloperoxidase," Free Radic Res 45(2):165-176, Elsevier Inc., United States (Feb. 2011).
Velsor, L.W., et al., "Antioxidant imbalance in the lungs of cystic fibrosis transmembrane conductance regulator protein mutant mice," Am J Physiol Lung Cell Mol Physiol 281(1):L31-L38, American Physiological Society, United States (Jul. 2001).
Venglarik, C.J., et al., "Hypochlorous acid alters bronchial epithelial cell membrane properties and prevention by extracellular glutathione," J Appl Physiol 95(6):2444-2452, American Physiological Society, United States (Dec. 2003).
Vilela, R.M., et al., "High hydrostatic pressure enhances whey protein digestibility to generate whey peptides that improve glutathione status in CFTR-deficient lung epithelial cells," Mol Nutr Food Res 50(11):1013-1029, Wiley-VCH Verlag, Germany (Nov. 2006).
Vilela, R.M., et al., "Inhibition of IL-8 release from CFTR-deficient lung epithelial cells following pre-treatment with fenretinide," Int Immunopharmacol 6(11):1651-1664, Elsevier, Netherlands (Nov. 2006).
Visca, A., et al., "Improvement in clinical markers in CF patients using a reduced glutathione regimen: an uncontrolled, observational study," J Cyst Fibros 7(5):433-436, Elsevier, Netherlands (Sep. 2008).
Wang, W., et al., "Reversible silencing of CFTR chloride channels by glutathionylation," J Gen Physiol 125(2):127-141, Rockefeller University Press, United States (Feb. 2005).
Ward, P.P., et al., "Lactoferrin and host defense," Biochem Cell Biol 80(1):95-102, National Research Council of Canada, Canada (2002).
Willing et al., "Shifting the balance: antibiotic effects on host-microbiota mutualism," Nature Reviews Microbiology 9(4):233-243 (2011) (Abstract Only).
Dewan "Advanced Drug Delivery Systems: Technologies and Global Markets," BCC Research Market Forecasting: 1-278 (2011).
Dewan "Global Markets for Orphan Drugs" BCC Research Market Forecasting: 1-212 (2013).
Highsmith "Biologic Therapeutic Drugs: Technologies and Global Markets," BCC Research Market Forecasting: 1-168 (2013).
Hancock, R.E.W., and Wong, P.G.W., "Compounds Which Increase the Permeability of the Pseudomonas aeruginosa Outer Membrane," Antimicrobial Agents and Chemotherapy, 26(1): 48-52, American Society for Microbiology, United States (Jul. 1984).
Hubert, D., et al., "Exhaled nitric oxide in cystic fibrosis: relationships with airway and lung vascular impairments," European Respiratory Journal, 34: 117-124, ERS Journal Ltd., Switzerland (Jul. 2009).
Fischer, H., et al., "Vitamin C controls the cystic fibrosis transmembrane conductance regulator chloride channel," PNAS, 101(10): 3691-3696, The National Academy of Science of the USA, United States (Mar. 2004).
Fischer, H., and Widdicombe, J.H., Mechanisms of Acid and Base Secretion by the Airway Epithelium, J Membr Biol 211(3): 139-150, Springer Science, Germany (2006).
Fisher, A. J., et al., "Cross sectional study of exhaled nitric oxide levels following lung transplantation," Thorax 53(6):454-458, British Thoracic Society, United Kingdom (Jun. 1998).
Jiao, J., et al., "The effects of vitamins C and B12 on human nasal ciliary beat frequency," BMC Complementary and Alternative Medicine 13(110): 1-6, Springer Nature, Berlin (May 2013).
Griese, M., et al., "Inhalation Treatment with Glutathione in Patients with Cystic Fibrosis," Am J Respir Crit Care Med 188(1): 83-89, The American Thoracic Society, United States (Jul. 2013).
Birket, S.E., et all., "A Functional Anatomic Defect of the Cystic Fibrosis Airway," Am J Respir Crit Care Med 190(4): 421-432, The American Thoracic Society, United States (Aug. 2014).
Liu, L., et al., "Method for Quantitative Study of Airway Functional Microanatomy Using Micro-Optical Coherence Tomography," PLOS One 8(1): e54473, Public Library of Science, United States (2013).
Liu, L., et al., "An Autoregulatory Mechanism Governing Mucociliary Transport Is Sensitive to Mucus Load," Am J Prespir Cell Mol Biol 51(4):485-93, The American Thoracic Society, United States (Oct. 2014).
Gabbay, E., et al., "Post-lung Transplant Bronchiolitis Obliterans Syndrome (BOS) is Characterized by Increase exhaled Nitric Oxide Levels and Epithelial Inducible Nitric Oxide Synthase," Am J Respir Crit Care Med 162(6):2182-2187,American Thoracic Society, United States (Dec. 2000).
Gaggar, A., et al., "The role of matrix metalloproteases in cystic fibrosis lung disease," Eur Respir J 38(3):721-727, European Respiratory Society, Switzerland (Sep. 2011).
Martinez-Alemán, S. R., "Understanding the entanglement: Neutrophil Extracellular Traps (NETs) in Cystic Fibrosis," Front Cell Infect Microbiol 7:104, Frontiers Media S.A., Switzerland (Apr. 2017).
Morice, A.H., "Airway reflux as a cause of respiratory disease," Breathe, 9(4): 256-266, European Respiratory Society, Switzerland (2013).
Tang, X., et al., "Acidic pH increases airways surface liquid viscosity in cystic fibrosis," J Clin Invest 126(3):879-891, American Society for Clinical Investigation, United States (Mar. 2016).
Tate, S., et al., "Airways in cystic fibrosis are acidified: detection by exhaled breath condensate," Thorax 57:926-929, BMJ Publishing Group Ltd & British Thoracic Society, United Kingdom (Nov. 2002).
Francoeur, C., and Denis, M., "Nitric oxide and interleukin-8 as inflammatory components of cystic fibrosis," Inflammation 19(5):587-598, Springer, Germany (Oct. 1995).
Dickerhof, N., et al., "Oxidative stress in early cystic fibrosis ling disease is exacerbated by airway glutathione deficiency," Free Radical Biology and Medicine 113: 236-243, Elsevier, Netherlands (Dec. 2017).
Kharitonov, S.A., et al., "Increased nitric oxide in exhaled air of asthmatic patients" The Lancet 343(8890): P133-P135, Elsevier, Netherlands (Jan. 1994).
Klare, W., et al., "Glutatione-disrupted biofilms of clinical Pseudomonas aeruginosa strains exhibit an enhanced antibiotic effect and a novel biofilm transcriptome," Antimicrob Agents Chemother 60(8):4539-4551, American Society for Microbiology, United States (Jul. 2016).
O'donnell, M.D., et al., "Treatment of Idiopathic Bronchiectasis With Aerosolized Recombinant Human DNase I," Chest 113(5):1329-1334, Elsevier, Netherlands (May 1998).
Paez, P.L., et al., "Effect of the association of reduced glutathione and ciprofloxacin on the antimicrobial activity in *Staphylococcus aureus*," FEMS Microbiol Lett 303(1):101-105, Oxford University Press, United Kingdom (Feb. 2010).
Rawal, B.D., et al., "Inhibition of Pseudomonas aeruginosa by ascorbic acid acting singly and in combination with antimicrobials: in-vitro and in-vivo studies," Med J Aust 1(6):169-174, John Wiley & Sons, United States (Feb. 1974).
Sakakura, Y., et al., "Mucociliary Function during experimentally Induced Rhinovirus Infection in Man," Ann Otol Rhinol Laryngol 82(2):203-211, SAGE Publications, United States (Mar.-Apr. 1973).
Vasilenko, A., "Antibacterial activity of glutathione in carbapenemase-producing Klebsiella pneumoniae and Pseudomonas aeruginosa," a Master's Thesis submitted to the Faculty of Richard L. Conolly College, Long Island University in fulfillment of the requirements for the degree of Masters of Science, May 2013, 52 pages.

(56) References Cited

OTHER PUBLICATIONS

Webassign, "Lab 10—Electrochemical Cells," General Chemistry II Labs, accessed at www.webassign.net/question_assets/ncsugenchem2021abv1/lab_10/manual.html, downloaded on Sep. 2, 2020, 8 pages.

De Villiers, B.L., et al., "Optimizing MCPA (K-salt) activity with adjuvants," South African Journal of Plant and Soil 17(2):63-65, Taylor and Francis Ltd., United Kingdom (2000).

Pedemonte, N., et al., "Thiocyanate Transport in Resting and IL-4 Stimulated Human Bronchial Epithelial Cells; Role of Pendrin and Anion Channels," J Immunol 178(8):5144-5153, American Association of Immunologists, United States (Apr. 2007).

Aliberti, S., et al., "Criteria and definitions for the radiological and clinical diagnosis of bronchiectasis in adults for use in clinical trials: international consensus recommendations," Lancet Respir Med 2600(21):1-9, Elsevier, Netherlands (Sep. 2021).

Chalmers, J. D., and Hill, A. T., "Mechanisms of immune dysfunction and bacterial persistence in non-cystic fibrosis bronchiectasis," Molecular Immunology 55(1):27-34, Elsevier, Netherlands (Aug. 2013).

Chalmers, J. D., et al., "Bronchiectasis," Nature Reviews Disease Primers 4:45, 18 pages, Nature Publishing Group, United Kingdom (Nov. 2018).

King, P. T., "The pathophysiology of bronchiectasis," Int J Chron Obstruct Pulmon Dis 4:411-419, Dove Press, New Zealand (Nov. 2009).

Nosotti, M., et al., "Infections after lung transplantation," Journal of Thoracic Disease 10(6):3849-3868, Pioneer Bioscience Publishing Company, Hong Kong (Jun. 2018).

Okamoto, K., and Santos, C. A. Q., "Management and prophylaxis of bacterial and mycobacterial infections among lung transplant recipients," Ann Transl Med 8(6):413, 12 pages, AME Publishing Company, China (Mar. 2020).

Schäfer, J., et al., "Pathogenesis, imaging and clinical characteristics of CF and non-CF bronchiectasis," BMC Pulm Med 18(1):79, 11 pages, BioMed Central Ltd., United Kingdom (May 2018).

Fux, C.A., et al., "Can laboratory reference strains mirror 'real-world' pathogenesis?," Trends Microbiol 13(2):58-63, Elsevier, Netherlands (Feb. 2005).

Grosso-Becerra, M-V., et al., "Pseudomonas aeruginosa clinical and environmental isolates constitute a single population with high phenotypic diversity," BMC Genomics 15(318):1-14, BioMed Central, United Kingdom (Apr. 2014).

Hanberger, H., et al., "Antibiotic Susceptibility Among Aerobic Gram-negative Bacilli in Intensive Care Units in 5 European Countries," JAMA 281 (1):67-71, American Medical Association, United States (Jan. 1999).

Hayes, D., et al., "Lung transplantation for advanced bronchiectasis," Semin Respir Crit Care Med 31(2):123-38, American Thoracic Society, United States (Apr. 2010).

Visscher, D.W., et al., "Bronchiolitis: the pathologist's perspective," Proc Am Thorac Soc 3(1):41-47, American Thoracic Society, United States (2006).

Saayman, S., et al., "Cystic Fibrosis Transmembrane Receptor Expression is Regulated by Long Antisense Non-Coding RNAs," Molecular Therapy 22, Supplement 1:S4, Cell Press, United States (May 2014).

Sodium Bicarbonate, PubChem ID 516892, accessed at https://pubchem.ncbi.nlm.nih.gov/compound/Sodium-bicarbonate, accessed on Oct. 6, 2022.

Ascorbic Acid, PubChem ID 54670067, accessed at https://pubchem.ncbi.nlm.nih.gov/compound/Ascorbic-acid, accessed on Oct. 6, 2022.

Glutathione, PubChem ID 124886, accessed at https://pubchem.ncbi.nlm.nih.gov/compound/Glutathione, accessed on Oct. 6, 2022.

Sass, R.L., and Scheuerman, R.F., "Sodium Bicarbonate, Entry for Nahcolite," in Handbook of Mineralogy, Mineral Data Publishing, United States (1962).

International Search Report and Written Opinion for International Application No. PCT/US2023/010081, mailed on Jun. 23, 2023, 10 pages.

Wullandri, P., et al., "Application of Modified Atmosphere Packaging (Map) on Fresh Fish," Squalen. 7(1): 39-49, Kementerian Kelautan dan Perikanan, Indonesia (May 2012).

Adewale, A,T., et al., "Novel Therapy of Bicarbonate, Glutathione, and Ascorbic Acid Improves Cystic Fibrosis Mucus Transport," American Journal of Respiratory Cell and Molecular Biology 63(3):362-373, American Thoracic Society, United States (Sep. 2020).

PubChem SID 439252008, create date, Dec. 19, 2020, p. 2 formula.

Behr, J., et al., "Evidence for Oxidative Stress in Bronchiolitis Obliterans Syndrome After Lung and Heart-lung Transplantation. The Munich Lung Transplant Group, " Transplantation 69(9):1856-1860, Lippincott Williams & Wilkins, United States (May 2000).

Borok, Md,Z., et al., "Effect of Glutathione Aerosol on Oxidant-antioxidant Imbalance in Idiopathic Pulmonary Fibrosis," The Lancet 338(8761):215-216, (Jun. 1991).

Donaldson, S,H., et al., "Mucus Clearance and Lung Function in Cystic Fibrosis With Hypertonic Saline," The New England Journal of Medicine 354(3):241-250, Boston, United States (Jan. 2006).

Elferink, J,G., et al., "Glutathione-induced Enhancement of Neutrophil Locomotion," Immunobiology 184(1):25-36, Elsevier, United Kingdom (Dec. 1991).

Henke, M,O., and Ratjen, F., "Mucolytics in Cystic Fibrosis," Paediatric Respiratory Reviews 8(1):24-29, W.B. Saunders, United Kingdom (Mar. 2007).

Meldrum, W,O., et al., "Mucin Gel Assembly is Controlled by a Collective Action of Non-mucin Proteins, Disulfide Bridges, Ca2+-mediated Links, and Hydrogen Bonding," Scientific Reports 8(1), (Apr. 2018).

Ramsey, K,A., et al., "Airway Mucus Hyperconcentration in Non-cystic Fibrosis Bronchiectasis," American Journal of Respiratory and Critical Care Medicine 201(6):661-670, American Thoracic Society, United States (Mar. 2020).

Yang, C., et al., "Dornase Alfa for Cystic Fibrosis," The Cochrane Database of Systematic Reviews 4:CD001127, Wiley, United Kingdom (Apr. 2016).

\* cited by examiner

AQUEOUS SOLUTION COMPRISING A GLUTATHIONE SALT

CROSS-REFERENCE TO RELATED APPLICATIONS

This application is a continuation of international application PCT/US2023/010081 filed Jan. 4, 2023, which claims the benefit of U.S. Provisional Application Ser. No. 63/296,405 filed Jan. 4, 2022, which are incorporated herein by reference in their entirety.

BACKGROUND

Field of the Disclosure

This disclosure relates to the general fields of chemistry and pharmaceutical preparations. In some aspects, the disclosure relates to pharmaceutical preparations, e.g., containing glutathione, suitable for delivery to the lung and methods of using the same. In some aspects, this disclosure provides pharmaceutical preparations and products relating to ARINA-1 for use in treating patients with chronic inflammatory lung diseases characterized by excess mucus and inflammation, such as lung transplant, cystic fibrosis (CF), non-CF bronchiectasis, chronic obstructive pulmonary disease (COPD), and other inflammatory lung diseases.

Background

Excess mucus and inflammation are hallmarks of chronic inflammatory lung diseases. Ion dysregulation contributes to excess mucus production and chronic, dysregulated inflammation, both of which result in lung damage and scarring that leads to lung failure. Ramsey et al., *American Journal of Respiratory and Critical Care Medicine* 201(6):661-670 (2020); Borok et al., *Lancet* 338:215-216 (1991); Behr et al., *Transplantation* 69:1856-1860 (2000). Glutathione is a critical antioxidant ion that contributes to the structural integrity of mucus (Meldrum et al., *Scientific Reports* 8(1): Article number 5802 (2018) https://doi.org/10.1038/s41598-018-24223-3) and regulates inflammatory responses. Elferink, *Immunobiology* 184(1):25-36 (1991). Chronic inflammation also leads to increased airway acidity that contributes to lung damage. Glutathione dysregulation and increased airway acidity directly contribute to hyperviscous mucus that is accompanied by delayed or absent mucociliary clearance and consequent obstruction of small and medium-sized airways. This results in a milieu that favors a feedback loop of bacterial colonization, chronic infection, and inflammation.

Current therapies for chronic inflammatory lung diseases include dornase alfa and hypertonic saline. Dornase alfa (Pulmozyme; Genentech Inc.), an inhaled recombinant human deoxyribonuclease that cleaves extracellular DNA accumulated in CF mucus, Yang et al., *Cochrane Database Syst Rev.* 4:CD001127 (2016). Hypertonic saline, which is believed to hydrate the mucus layer through osmotically driven fluid transfer. Donaldson et al., *N Engl J Med.* 354:241-250 (2006). However, improvements in lung function, exacerbations, and quality of life observed with these agents are modest and variable. Yang et al., *Cochrane Database Syst Rev.* 4:CD001127 (2016); Henke et al., *Paediatr Respir Rev.* 8:24-29 (2007).

ARINA-1 is a compounded pharmaceutical preparation used to treat CF and other chronic inflammatory lung diseases. ARINA-1 is prepared by dissolving bicarbonate, L-glutathione, and ascorbic acid in water. The aqueous solution thus obtained is nebulized prior to administration to the lung of the patient. See, e.g., Adewale et al., *Am J Respir Cell Mol Biol.* 63:362-373 (2020); U.S. Pat. Nos. 9,308,234 and 11,058,743; and U.S. Patent Appl. Nos. 2019/0351005 and 2020/0397849. There exists a need in the art for stable pharmaceutical preparations and products for use in lung disease therapy.

BRIEF SUMMARY

This disclosure provides stable pharmaceutical preparations and products relating to ARINA-1 for use in treating patients with chronic inflammatory lung diseases characterized by excess mucus and inflammation, such as lung transplant, cystic fibrosis (CF), non-CF bronchiectasis, chronic obstructive pulmonary disease (COPD), and other inflammatory lung diseases.

The compounding of ARINA-1 and related pharmaceutical preparations comprises dissolving a bicarbonate salt, e.g., sodium bicarbonate, L-glutathione, and ascorbic acid in water. Applicant has discovered that such aqueous compositions are surprisingly stable when prepared, packaged, and stored under an atmosphere of carbon dioxide.

In one aspect, the disclosure provides a preparation comprising an aqueous solution in a closed container with a headspace, wherein:
(i) the aqueous solution comprises a salt having Formula I:

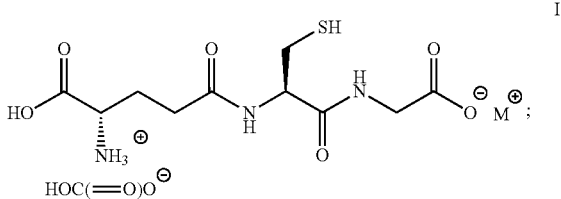

(ii) the atmosphere of the headspace comprises 90% or more carbon dioxide by volume; and
(iii) $M^+$ is $Na^+$, $Li^+$, $K^+$ or $Cs^+$.

In another aspect, the disclosure provides a method of making a preparation comprising the aqueous solution comprising a salt having Formula I, the method comprising:
(i) dissolving L-glutathione, ascorbic acid, and $M^+HCO_3^-$, wherein $M^+$ is $Na^+$, $Li^+$, $K^+$ or $Cs^+$, in water for injection under an atmosphere of carbon dioxide to give an aqueous solution;
(ii) transferring a portion of the aqueous solution to a container;
(iii) overlaying the aqueous solution with carbon dioxide; and
(iv) sealing the container with a stopper.

In another aspect, the disclosure provides an aqueous solution comprising a salt having Formula I prepared by dissolving L-glutathione, ascorbic acid, and $M^+HCO_3^-$, wherein $M^+$ is $Na^+$, $Li^+$, $K^+$ or $Cs^+$, in water for injection under an atmosphere of carbon dioxide.

DETAILED DESCRIPTION

I. Preparations of the Disclosure

Figure 1:
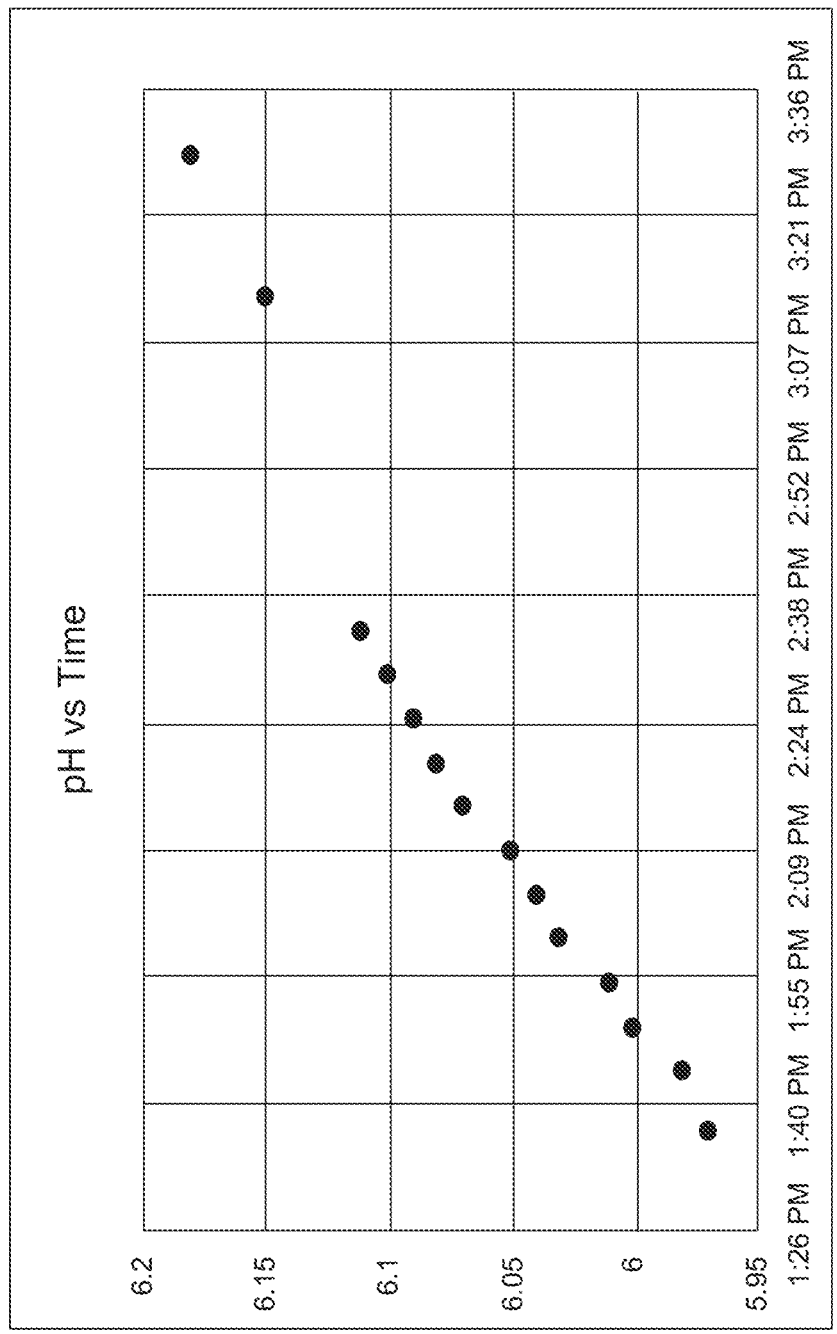
FIG. 1 is a line graph showing the pH versus time of an aqueous solution comprising sodium bicarbonate, L-glutathione, and ascorbic acid compounded under an atmosphere of nitrogen.

In one aspect referred to as "Embodiment I," the present disclosure provides a preparation comprising an aqueous solution in a closed container with a headspace, wherein:

(i) the aqueous solution comprises a salt having Formula I:

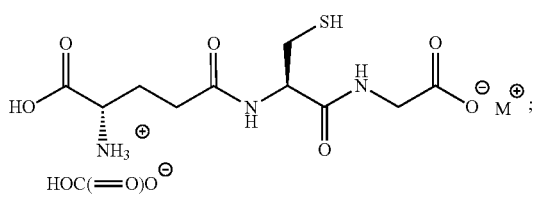

(ii) the atmosphere of the headspace comprises 90% or more carbon dioxide by volume; and (iii) $M^+$ is $Na^+$, $Li^+$, $K^+$ or $Cs^+$.

In another aspect, the aqueous solution of Embodiment I has a pH of 6.0±0.4 for 24 hours or more at about 5° C.

In another aspect, the aqueous solution of Embodiment I has a pH of 6.0±0.3 for 24 hours or more at about 5° C.

In another aspect, the aqueous solution of Embodiment I has a pH of 6.0±0.2 for 24 hours or more at about 5° C.

In another aspect, the aqueous solution of Embodiment I has a pH of 6.0±0.1 for 24 hours or more at about 5° C.

In another aspect, the aqueous solution of Embodiment I further comprises a salt having Formula II:

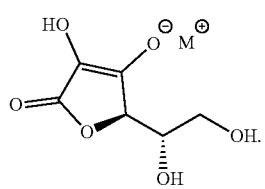

In another aspect, the aqueous solution of Embodiment I further comprises a salt having Formula III:

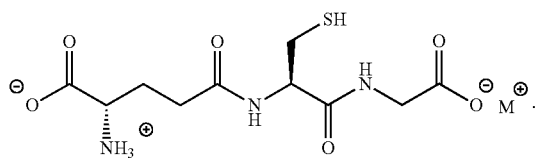

In another aspect, the atmosphere of the headspace of Embodiment I comprises 80% or more of carbon dioxide by volume.

In another aspect, the atmosphere of the headspace of Embodiment I comprises 85% or more of carbon dioxide by volume.

In another aspect, the atmosphere of the headspace of Embodiment I comprises 90% or more of carbon dioxide by volume.

In another aspect, the atmosphere of the headspace of Embodiment I comprises 95% or more of carbon dioxide by volume.

In another aspect, the aqueous solution of Embodiment I comprises about 10 wt % to about 20 wt % of the salt having Formula I.

In another aspect, the aqueous solution of Embodiment I comprises about 13 wt % to about 17 wt % of the salt having Formula I.

In another aspect, the aqueous solution of Embodiment I comprises about 14.7 wt % of the salt having Formula I.

In another aspect, the aqueous solution of Embodiment I comprises about 5 wt % to about 15 wt % of the salt having Formula II.

In another aspect, the aqueous solution of Embodiment I comprises about 7 wt % to about 11 wt % of the salt having Formula II.

In another aspect, the aqueous solution of Embodiment I comprises about 9.1 wt % of the salt having Formula II.

In another aspect, the aqueous solution of Embodiment I has a density of about 1.13 g/L.

In another aspect, the aqueous solution of Embodiment I is frozen.

In another aspect, $M^+$ is $Na^+$ in Embodiment I.
In another aspect, $M^+$ is $Li^+$ in Embodiment I.
In another aspect, $M^+$ is $K^+$ in Embodiment I.
In another aspect, $M^+$ is $Cs^+$ in Embodiment I.

In another embodiment, the preparation of Embodiment I is packaged as a single unit dose. In another aspect, the single unit dose is in a sealed vial.

In another aspect, the preparation of Embodiment I is marketed, distributed, or administered as part of a pharmaceutical product.

In some aspects, the preparation of Embodiment I can further comprise any one or more of the further aspects disclosed herein.

II. Methods of Making a Preparation

In another aspect referred to as "Embodiment II," the present disclosure provides a method of making the preparation of Embodiment I (or Embodiment I including one or more the further aspects disclosed above), the method comprising:

(i) dissolving L-glutathione, ascorbic acid, and $M^+HCO_3^-$, wherein $M^+$ is $Na^+$, $Li^+$, $K^+$ or $Cs^+$, in water for injection under carbon dioxide to give an aqueous solution;

(ii) transferring a portion of the aqueous solution to a container;
(iii) overlaying the aqueous solution with carbon dioxide; and
(iv) sealing the container with a stopper.

In another embodiment, about 8 wt % to about 18 wt % of L-glutathione, about 3 wt % to about 13 wt % of ascorbic acid, and about 3 wt % to about 13 wt % of $M^+HCO_3^-$ is dissolved in about 62 wt % to about 82 wt % water for injection to give the aqueous solution of Embodiment II.

In another aspect, the aqueous solution of Embodiment II has a pH of 6.0±0.4 for 24 hours or more at about 5° C.

In another aspect, the aqueous solution of Embodiment II has a pH of 6.0±0.3 for 24 hours or more at about 5° C.

In another aspect, the aqueous solution of Embodiment II has a pH of 6.0±0.2 for 24 hours or more at about 5° C.

In another aspect, the aqueous solution of Embodiment II has a pH of 6.0±0.1 for 24 hours or more at about 5° C.

In another aspect, $M^+$ is $Na^+$, i.e., $M^+HCO_3^-$ is sodium bicarbonate, in Embodiment II.

In another aspect, $M^+$ is $Li^+$, i.e., $M^+HCO_3^-$ is lithium bicarbonate, in Embodiment II.

In another aspect, $M^+$ is $K^+$, i.e., $M^+HCO_3^-$ is potassium bicarbonate, in Embodiment II.

In another aspect, $M^+$ is $Cs^+$, i.e., $M^+HCO_3^-$ is cesium bicarbonate, in Embodiment II.

In another aspect, about 11 wt % to about 15 wt % of L-glutathione, about 5 wt % to about 9 wt % of ascorbic acid, and about 5 wt % to about 9 wt % of sodium bicarbonate is dissolved in about 68 wt % to about 76 wt % water to give the aqueous solution of Embodiment II, wherein $M^+$ is $Na^+$.

In another aspect, about 13.0 wt % of L-glutathione, about 7.6 wt % of ascorbic acid, and about 7.3 wt % of sodium bicarbonate is dissolved in about 72.0 wt % water to give the aqueous solution of Embodiment II, wherein $M^+$ is $Na^+$.

In some aspects, the method of Embodiment II can further comprise any one or more of the further aspects disclosed herein.

III. Product by Process

In another aspect referred to as "Embodiment III," the present disclosure provides an aqueous solution comprising a salt having Formula I:

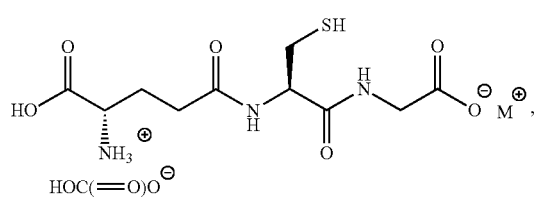

prepared by dissolving L-glutathione, ascorbic acid, and $M^+HCO_3^-$, wherein $M^+$ is $Na^+$, $Li^+$, $K^+$ or $Cs^+$, in water for injection under an atmosphere of carbon dioxide.

In another aspect, about 8 wt % to about 18 wt % L-glutathione, about 3 wt % to about 13 wt % of ascorbic acid, and about 3 wt % to about 13 wt % $M^+HCO_3^-$ is dissolved in about 62 wt % to about 82 wt % water for injection to give the aqueous solution of Embodiment III.

In another aspect, the aqueous solution of Embodiment III has a pH of 6.0±0.4 for 24 hours or more at about 5° C.

In another aspect, the aqueous solution of Embodiment III has a pH of 6.0±0.3 for 24 hours or more at about 5° C.

In another aspect, the aqueous solution of Embodiment III has a pH of 6.0±0.2 for 24 hours or more at about 5° C.

In another aspect, the aqueous solution of Embodiment III has a pH of 6.0±0.1 for 24 hours or more at about 5° C.

In another aspect, the aqueous solution of Embodiment III further comprises a salt having Formula II:

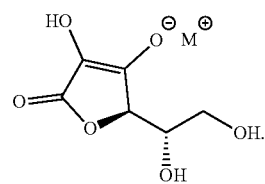

In another aspect, the aqueous solution of Embodiment III further comprises a salt having Formula III:

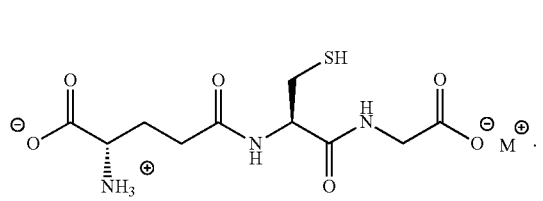

In another aspect, $M^+$ is $Na^+$, i.e., $M^+HCO_3^-$ is sodium bicarbonate, in Embodiment III.

In another aspect, $M^+$ is $Li^+$, i.e., $M^+HCO_3^-$ is lithium bicarbonate, in Embodiment III.

In another aspect, $M^+$ is $K^+$, i.e., $M^+HCO_3^-$ is potassium bicarbonate, in Embodiment III.

In another aspect, $M^+$ is $Cs^+$, i.e., $M^+HCO_3^-$ is cesium bicarbonate, in Embodiment III.

In another aspect, about 11 wt % to about 15 wt % L-glutathione, about 5 wt % to about 9 wt % of ascorbic acid, and about 5 wt % to about 9 wt % sodium bicarbonate is dissolved in about 68 wt % to about 76 wt % water to give the aqueous solution in Embodiment III.

In another aspect, about 13.0 wt % L-glutathione, about 7.6 wt % ascorbic acid, and about 7.3 wt % sodium bicarbonate is dissolved in about 72.0 wt % water to give the aqueous solution in Embodiment III.

In some aspects, the aqueous solution of Embodiment III can further comprise any one or more of the further aspects disclosed herein.

IV. Methods of Use

The preparations or aqueous solutions disclosed herein including those described above in Sections I-II (e.g., Embodiment I and III, and further aspects thereof) are useful for treating, reducing the symptoms of, or preventing a variety of diseases, conditions, or disorders. In particular, these preparations and aqueous solutions are useful in therapeutic methods of treating, reducing the symptoms of, or preventing a disease, condition, or disorder wherein the administration of L-glutathione, or a salt thereof, and/or ascorbic acid, or a salt thereof, provides a benefit.

In one aspect, the methods of treating or preventing a pulmonary or airway disorder in a subject in need thereof comprises administering, e.g., via inhalation, to the subject a therapeutically effective amount of a preparation described in Section I or an aqueous solution described in Section III.

In one aspect, the pulmonary or airway disorder is selected from the group consisting of chronic inflammatory lung disease, pulmonary fibrosis, pulmonary vasculitis, pulmonary sarcoidosis, an inflammation and/or infection associated with lung transplantation, acute or chronic lung acute or chronic rejection, chronic lung allograft dysfunction (CLAD, pulmonary artery hypertension, bronchitis, sinusitis, asthma, cystic fibrosis, a bacterial infection, a fungal infection, a parasite infection, a viral infection, chronic obstructive pulmonary disease (COPD), bronchiolitis obliterans syndrome (BOS), primary ciliary dyskinesia (PCD), alveolar proteinosis, idiopathic pulmonary fibrosis, eosinophilic pneumonia, eosinophilic bronchitis, acute respiratory distress syndrome (ARDS), an inflammation and/or infection associated with mechanical ventilation, ventilator-associated pneumonia, complications associated with acute or chronic placement of a tracheostomy, an asbestos-related airway disorder or disease, a dust-related airway disorder or disease, silicosis, and a radiation or chemical agent-related airway disease or disorder, and any combination thereof.

In another aspect, the pulmonary or airway disorder is selected from the group consisting of chronic inflammatory lung disease, an inflammation and/or infection associated with lung transplantation, acute or chronic lung rejection, chronic lung allograft dysfunction (CLAD), asthma, cystic fibrosis, and chronic obstructive pulmonary disease (COPD), compilations associated with acute or chronic tracheostomy placement, and any combination thereof. In another embodiment, the method further comprises administering an additional therapeutic agent to the subject.

In another aspect, the pulmonary or airway disorder arises collaterally from radiation and/or chemotherapy in subjects having cancer.

In another aspect, the present disclosure provides methods of treating or preventing an infection in the airway of a subject in need thereof, the method comprising administering to the subject a therapeutically effective amount of a preparation described in Section I. In another embodiment, a preparation described in Section I is administered to the subject in combination with one or more antibiotics. The antibiotics can be administered locally to the lungs and/or systemically.

In another aspect, the present disclosure provides methods of treating or preventing inflammation in the airway of a subject in need thereof, the method comprising administering to the subject a preparation described in Section I.

In another aspect, the present disclosure provides methods of treating or preventing a disease or disorder in mucosal tissue in a subject in need thereof, the method comprising administering to the subject a therapeutically effective amount of a preparation described in Section I. Non-limiting examples of mucosal tissue include the mouth, nose, eye, ear, upper respiratory tract, lower respiratory tract, gastrointestinal tract, vagina, rectum and urethra.

In another aspect, the present disclosure provides methods of treating or preventing a disease or disorder associated with mucosal membranes, in a subject in need thereof, the method comprising administering to the subject a therapeutically amount of a preparation described in Section I to the appropriate mucosal membranes. In one embodiment, the mucosal membranes are the lungs, such the mid-bronchioles or the deep lung (alveolar region), and in other embodiments, the mucosal membranes are one or more of the eyes, mouth, nose, rectum, urogenital tract, and vagina.

In another aspect, a preparation described in Section I is used to treat or prevent bronchiolitis obliterans and military-related lung damage, i.e., lung damage of military personnel who have damaged airways secondary to unknown exposures.

The therapeutic methods of this disclosure comprise administering a therapeutically effective amount of a preparation described in Section I to a subject in need thereof, e.g., a human patient. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

In some aspect, a preparation described in Section I is nebulized prior to administration to a subject.

V. Definitions

The term "ARINA-1" refers to the pharmaceutical preparation obtained by combining L-glutathione, ascorbic acid, and sodium bicarbonate in water to give the aqueous solution. The chemical entities present in ARINA-1 when prepared and maintained under an atmosphere of $CO_2$ may include sodium L-ascorbate, L-glutathione sodium/bicarbonate salt, and L-glutathione sodium as shown in Scheme 1.

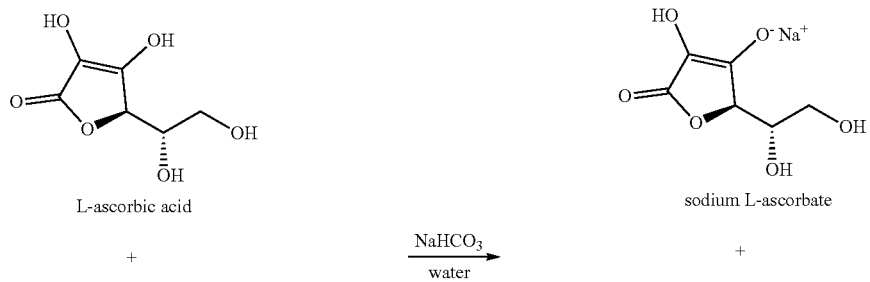

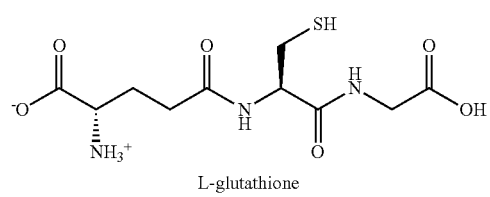

L-glutathione

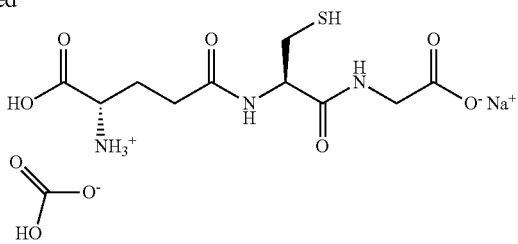

L-glutathione sodium/bicarbonate salt
(predominant component)

+

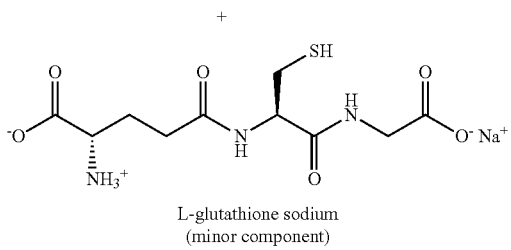

L-glutathione sodium
(minor component)

The stoichiometry of the components of ARINA-1 is shown in Table 1.

TABLE 1

| Formulation | Mol. Wt. | amount (g) | Moles | Rel. Equiv. |
|---|---|---|---|---|
| L-glutathione reduced | 307.32 | 150.0 | 0.488 | 1.00 |
| L-ascorbic acid | 176.12 | 88.0 | 0.500 | 1.02 |
| sodium bicarbonate | 84.01 | 84.0 | 1.000 | 2.05 |
| water | | 829.0 | | |

The term "pharmaceutical product" refers to a product suitable for human use. In some aspects, the pharmaceutical product is suitable for human use and is subject to regulation by the United States Food and Drug Administration (FDA) or a foreign equivalent of the FDA including, but not limited to, the European Medicines Agency (EMA), the National Medical Products Administration (NMPA) of China, and the Japanese Ministry of Health Labor and Welfare (MHLW).

The term "preparation" refers to one or more drugs intended for human use that is either (i) in its finished dosage form; or (ii) to be used for the preparation, formulation, and/or administration of the finished dosage form.

The term "container" refers to a pharmaceutically acceptable container comprising a chamber suitable to house an aqueous solution comprising one or more drug products. The "closed end" of the container refers to the end of the chamber having no opening. The term "open end" of the container refers to the end of the chamber opposite the closed end. Exemplary containers include, but are not limited to, vials, syringes, cartridges, bags, e.g., polypropylene and polyurethane bags, and ampoules. In one embodiment, the container is a vial.

The term "stopper" as used herein refers to any article capable of preventing an aqueous solution and a gas, e.g., carbon dioxide, from exiting the open end of a container.

The term "closed container" as used herein refers to a container affixed with a stopper.

The term "headspace" as used herein refers to the area within the chamber of a container between an aqueous solution and a stopper when the open end of the container is oriented away from the pull of gravity.

The term "atmosphere" as used herein refers to the layer of one or more gases in the headspace of a closed container. These gases include, but are not limited to oxygen, nitrogen, argon, and carbon dioxide. In one embodiment, the atmosphere in the pharmaceutical product of the present disclosure comprises 75% carbon dioxide or more, e.g., 80% carbon dioxide or more, 85% carbon dioxide or more, 90% carbon dioxide or more, 95% carbon dioxide or more, or 99% carbon dioxide or more, by volume.

The term "wt %" as used herein in connection with an aqueous solution refers to the mass of one component divided by the combined mass of all components (including, e.g., the water for injection) times 100. For example, the wt % of L-glutathione sodium/bicarbonate salt, i.e., a compound of Formula I, wherein $M^+$ is $Na^+$, in an aqueous solution comprising 161 g of L-glutathione sodium/bicarbonate salt, 99 g of sodium ascorbate, i.e., a compound of Formula II, wherein $M^+$ is $Na^+$, 1 gram of sodium bicarbonate, and 829 g of water is 14.8 wt % (161 g/1090 g=0.148×100=14.8 wt %). Likewise, the wt % of L-glutathione when 150 g of L-glutathione, 88 g of ascorbic acid, and 84 g of sodium bicarbonate is dissolved in 829 g of water to give an aqueous solution is 13.0 wt % (150 g/1151 g=0.130×100=13.0 wt %).

The terms "a" and "an" refer to one or more than one.

The term "about," as used herein, includes the recited number+10%. Thus, "about 10" means 9 to 11.

EXAMPLES

General Methods

Materials

L-ascorbic acid (Lot #1200851004) and L-glutathione reduced (Lot #B200465) used in the 2-L scale experiment were sourced from CSPC Weisheng Pharmaceutical (Shijiazhuang) Co. and Shandong Jincheng Biopharmaceutical Co., respectively. L-ascorbic acid (Product #A92902) and L-glutathione reduced (Product #G4251) used in the 0.75-L scale experiment run involving carbon dioxide blanketing were purchased from Millipore Sigma Co. Sodium bicarbonate (Product #S6014) for all trials was purchased from Millipore Sigma Co. Deionized water was provided from a Millipore water system. All other raw materials and solvents used to analyze the product were purchased from commercial vendors and used as received.

NMR Instrumentation

NMR was employed to assess the titer of L-ascorbic acid, L-glutathione reduced, L-glutathione disulfide and any unknown impurities in the demonstration runs. 1H NMR spectra were obtained at 25° C. using a Bruker Avance III 500 MHz NMR system, equipped with a 5-mm, triple-resonance Cryoprobe. Deuterium oxide was used as the NMR solvent, and the resonance from calcium formate was used as a reference to establish chemical shift and integration values. NMR spectral data were processed using MNova software.

Example 1

Compounding of ARINA-1 Under $N_2$

A 2-L scale preparation of ARINA-1, see Table 2, was carried out in a jacketed 4-neck glass reactor fitted with an overhead stirrer, a thermometer, a gas inlet adapter, a port for solids charging, and a second adapter to constrict the flow of nitrogen leaving the flask via a Claisen adapter. Nitrogen was charged to the flask via a flow meter capable of measuring flow between 0.05-0.5 L/min. Temperature control of the reaction was achieved by recirculating a water/glycol mixture from the vessel jacket into a Haake EZ-Cool 80 recirculating heater/chiller.

TABLE 2

| Formulation | MW | amount (g) | Moles | Rel. Equiv. |
|---|---|---|---|---|
| glutathione | 307.32 | 300.0 | 0.976 | 1.00 |
| Ascorbic acid | 176.12 | 176.0 | 0.999 | 1.02 |
| sodium bicarbonate | 84.01 | 168.0 | 2.000 | 2.05 |
| water | | 1600.0 | | |
| water rinse | | 58.0 | | |
| TOTAL MASS ADDED | | 2244.0 | | |
| $O_2$ | 32 | 0.009 | 0.001125 | 0.12% |
| | 32 | 0.001 | 0.00003125 | 0.01% |

The pH was monitored at the end of L-glutathione neutralization, and an upward increase in pH was measured to be about +0.1 pH unit per hour at the temperatures (° C.) indicated in Table 3 and FIG. 1

TABLE 3

| pH | | temp |
|---|---|---|
| 1:38 PM | 5.97 | 18.4 |
| 1:45 PM | 5.98 | 16.5 |
| 1:50 PM | 6.00 | 14.7 |
| 1:55 PM | 6.01 | 12.9 |
| 2:00 PM | 6.03 | 11.4 |
| 2:05 PM | 6.04 | 10.0 |
| 2:10 PM | 6.05 | 8.7 |
| 2:15 PM | 6.07 | 7.7 |
| 2:20 PM | 6.08 | 6.7 |
| 2:25 PM | 6.09 | 5.9 |
| 2:30 PM | 6.10 | 5.0 |
| 2:35 PM | 6.11 | 4.0 |
| 2:40 PM | | |
| 3:13 PM | 6.15 | −1.7 |
| 3:29 PM | 6.18 | −2.3 |

Example 2

Compounding of ARINA-1 Under $CO_2$

Figure 4:
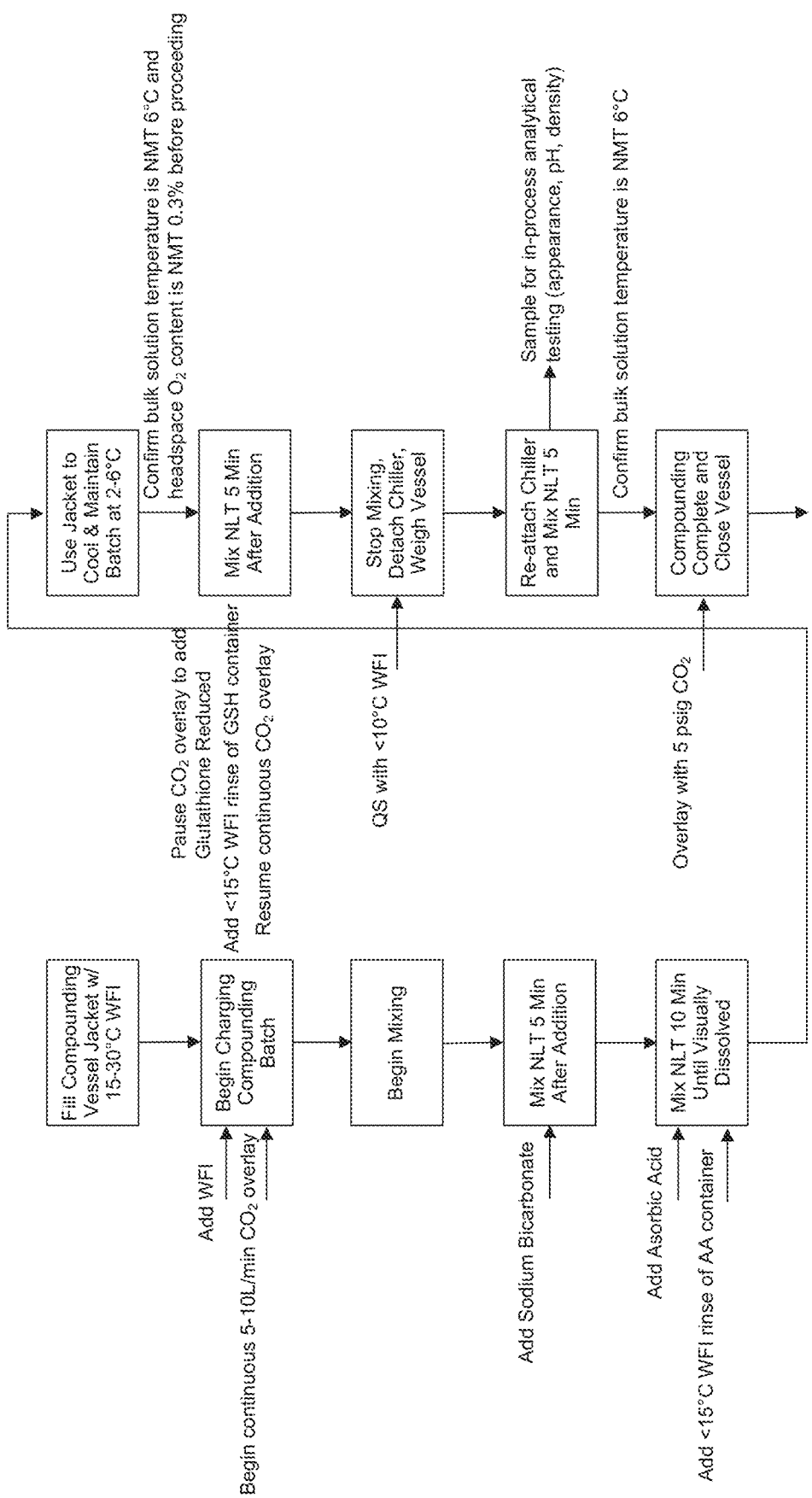
FIG. 4 is a flow diagram showing the compounding steps used to prepare ARINA-1 under an atmosphere of carbon dioxide.

A 750-mL scale preparation of ARINA-1, see Table 4, was carried out in a 1-L jacketed 4-neck glass reactor fitted with an overhead stirrer, a thermometer, a gas inlet adapter, a port for solids charging. Carbon dioxide was charged to the reactor via a gas flow meter capable of measuring between 0.05-0.5 L/min. Temperature control of the reaction was achieved by recirculating a water/glycol mixture between the vessel jacket and a Haake EZ-Cool 80 recirculating heater/chiller. The compounding process steps are outlined in FIG. 4.

TABLE 4

| Formulation | MW | amount (g) | Moles | Rel. Equiv. |
|---|---|---|---|---|
| glutathione | 307.32 | 112.5 | 0.366 | 1.00 |
| Ascorbic acid | 176.12 | 66.0 | 0.375 | 1.02 |
| sodium bicarbonate | 84.01 | 63.0 | 0.750 | 2.05 |
| water | | 600.0 | | |
| water #2 | | 21.75 | | |
| TOTAL MASS ADDED | | 841.5 | | |

Process Description:
1. Added 600 g of deionized water to the reactor. This amount of water, along with the rinse introduced in step 6, gave a product density of 1.12 to 1.13 g/mL. Began agitation by setting the overhead stirrer rate to about 90-100 rpm. The temperature of the water in the demonstration trial was 21° C.
2. Added 63.0 g of sodium bicarbonate and continued agitation for about 10 minutes to allow most of the sodium bicarbonate to dissolve.
3. Displaced air in the headspace of the flask completely using gaseous carbon dioxide from a cylinder source fitted with an appropriate gas regulator.
4. Charged 66.0 g of L-ascorbic acid to the flask at a rate that ensured controlled evolution of carbon dioxide gas. Once the solid addition was done, the reaction was complete within 2-3 minutes resulting in a clear solution, after which time step 5 may commence.
5. Charged 112.5 g of L-glutathione reduced to the flask at a rate that ensured controlled evolution of carbon dioxide gas. Reaction was complete within 4-5 minutes following the last solid addition, resulting in a clear solution.
6. Measured out 21.75 g of deionized water, and used it to rinse any solids remaining in the solids addition funnel and/or the upper vessel wall that may have adhered solids present. Increased the rate of agitation dramatically and held for 10-15 seconds to splash any solid or liquid clinging to the vessel wall in order to achieve a completely homogeneous mixture.

7. Returned to a slower rate of agitation (but maintained an agitation rate sufficient to promote heat transfer) and immediately cooled the solution to between 2 to 6° C.

Figure 2:
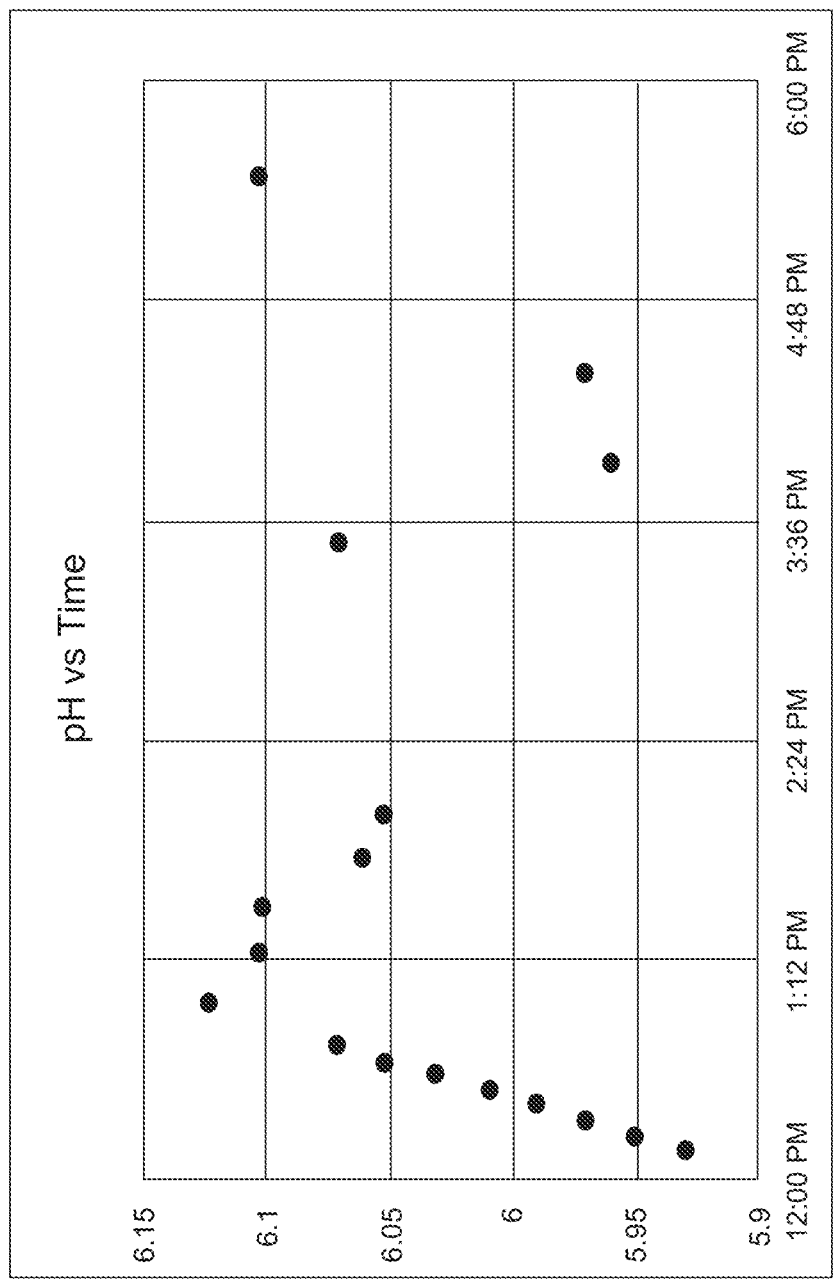
FIG. 2 is a line graph showing the pH versus time of an aqueous solution comprising sodium bicarbonate, L-glutathione, and ascorbic acid compounded under an atmosphere of carbon dioxide.

The pH was monitored at the end of L-glutathione neutralization at the temperatures (° C.) indicated in Table 5 and FIG. 2.

TABLE 5

| | pH | temp |
|---|---|---|
| 12:10 PM | 5.93 | 14.5 |
| 12:15 PM | 5.95 | 13.3 |
| 12:20 PM | 5.97 | 11.5 still slowly bubbling |
| 12:25 PM | 5.99 | 9.6 |
| 12:30 PM | 6.01 | 8.0 bubbling barely evident |
| 12:35 PM | 6.03 | 6.7 |
| 12:40 PM | 6.05 | 5.4 no bubbling evident |
| 12:45 PM | 6.07 | 3.5 |
| 1:00 PM | 6.12 | 0.0 |
| 1:15 PM | 6.10 | 0.0 |
| 1:30 PM | 6.10 | 0.0 bath temp increased to 5 deg |
| 1:45 PM | 6.06 | 4.1 |
| 2:00 PM | 6.05 | 3.3 |
| 3:30 PM | 6.07 | 0.0 bath set to 15 deg |
| 3:55 PM | 5.96 | 13.8 slow bubbling returned |
| 4:25 PM | 5.97 | 15.0 bath temp returned to 1 deg C. |
| 5:30 PM | 6.10 | 1.0 |
| 10:00 AM next day | 6.00 | 4.0 |

The issue with continuous sparge or sweep of nitrogen in EXAMPLE 1 is that the nitrogen flow strips residual $CO_2$ out of the system, which in turn drives the decomposition of carbonic acid formed by the neutralization reactions. This increases pH above the target range of pH 5.8-6.4. In an experiment using a slow nitrogen sweep, the pH of the compounded product rose from 6.0 to 7.3 after approximately 18 hours of post-reaction inerting (data not shown).

Henry's gas law states that the amount of dissolved gas in a liquid is proportional to its partial pressure above the liquid. The partial pressure of $CO_2$ in the headspace above the product solution is kept close to zero under the condition of a slow, continuous nitrogen sweep. If, however, gaseous $CO_2$ is used to inert the headspace, the pressure of $CO_2$ becomes 1 atmosphere, which should provide a driving force to reverse $CO_2$ loss and establish an equilibrium that stabilizes pH. This principle was demonstrated in this example.

Figure 3:
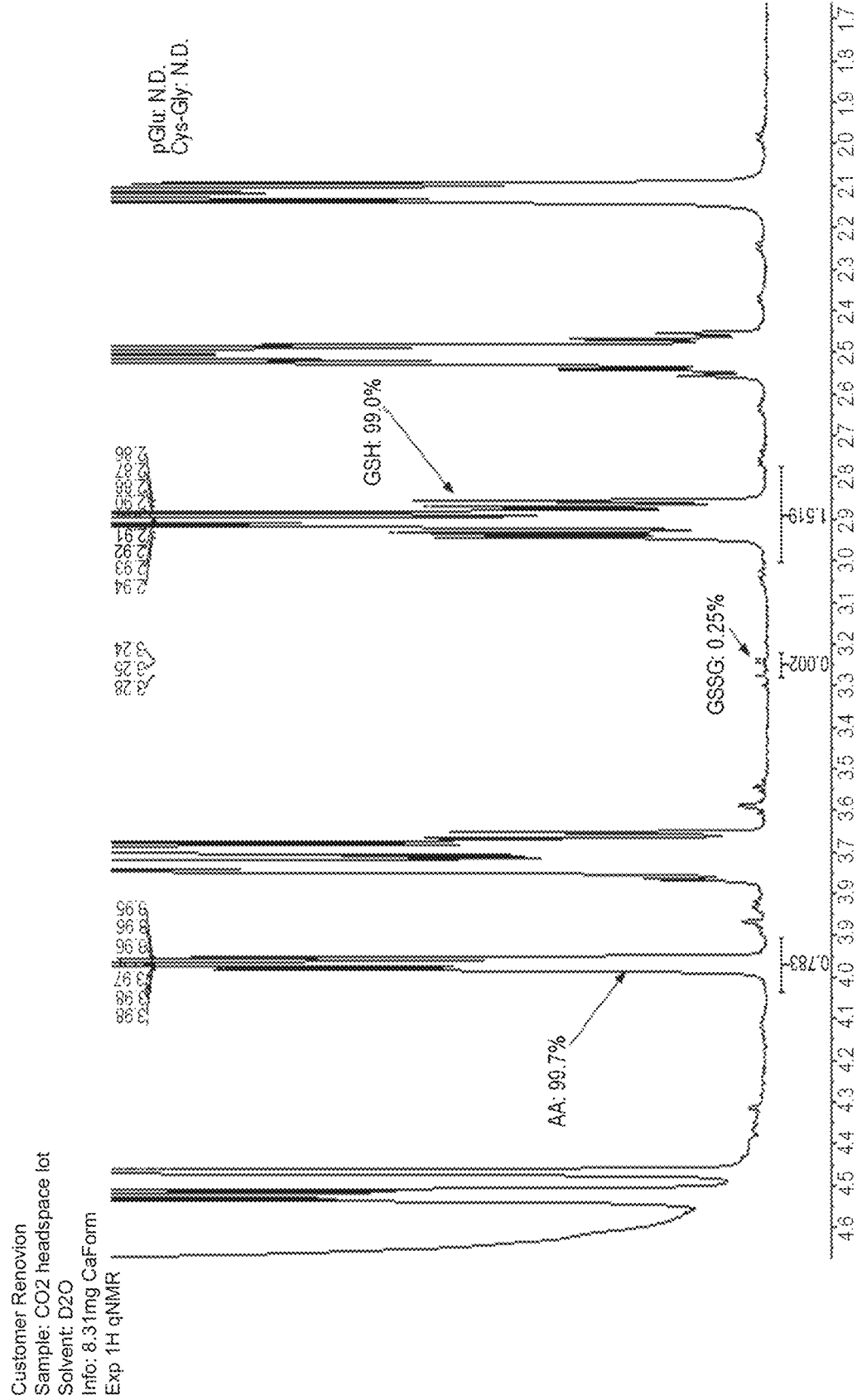
FIG. 3 is a partial NMR spectrum of an aqueous solution comprising sodium bicarbonate, L-glutathione, and ascorbic acid compounded under an atmosphere of carbon dioxide.

L-glutathione reduced is an acid that is being neutralized by sodium bicarbonate, and that gaseous $CO_2$ evolution should not be expected to stop until an equilibrium is established between the dissolved $CO_2$ in solution and $CO_2$ in the headspace. As in prior runs under, e.g., nitrogen, the pH rose following solid dissolution from about 5.95 to 6.10 while gas evolution was still evident as the solution was being cooled to 2-6° C. Equilibrium was established once the target pH range of 6.0-6.1 was reached. Raising the temperature and lowering it over the next 4 hours of the experiment did not have a significant effect on pH. After the solution was maintained under a slight positive pressure of $CO_2$ over 20+ hours a pH of 6.0 was again obtained. The solution was sampled for NMR analysis and gave assay values of 99.7 and 99.0% for L-ascorbic acid and L-glutathione reduced, respectively. See FIG. 3. The disulfide level was 0.25%, and no unexpected resonances were found that would indicate unaccounted degradants at or above 0.2% level. The use of a $CO_2$ blanket thus unexpectedly stabilizes the pH at its target range, as needed to permit consistency of product pH (and $CO_2$ content) throughout the vial filling cycle, while also excluding oxygen and controlling disulfide formation.

All inputs to this example were carefully measured by weight, permitting an analysis of the actual product $CO_2$ content that corresponds to pH 6.1. As shown in the stoichiometry calculations below for a 1-L preparation of ARINA-1, if all $CO_2$ were to have been expelled the product should be expected to weigh 1107.6 g, while if all $CO_2$ were unexpectedly retained in solution the product should weigh 1151.0 g. A 500-mL portion of preparation of this example was weighed and found to be 1125.8 g/L.

| Formulation | Mol. Wt. | amount (g) | Moles | Rel. Equiv. |
|---|---|---|---|---|
| glutathione | 307.32 | 150.0 | 0.488 | 1.00 |
| Ascorbic acid | 176.12 | 88.0 | 0.500 | 1.02 |
| sodium bicarbonate | 84.01 | 84.0 | 1.000 | 2.05 |
| water | | 800.0 | | |
| water #2 (rinse) | | 29 | | |

↓ (post-neutralization)

| Formulation | Mol. Wt. | amount (g) | Moles | Rel. Equiv. |
|---|---|---|---|---|
| Na glutathionate generated | 329.3 | 160.7 | 0.488 | 1.00 |
| Na ascorbate generated | 198.1 | 99.1 | 0.500 | 1.02 |
| sodium bicarbonate remaining | 84.01 | 1.0 | 0.012 | 0.02 |
| water | | 800.0 | | |
| water #2 (rinse) | | 29 | | |
| water generated from bicarbonate | 18.02 | 17.8 | 0.988 | |
| CO2 potentially lost | 44 | 43.5 | 0.988 | |
| TOTAL MASS - if all CO2 lost | | 1107.6 | | |
| TOTAL MASS - if no CO2 lost | | 1151.0 | | |
| TOTAL MASS - actually measured | | 1125.8 | | |
| Difference (as H2CO3) | 62.02 | 18.2 | 0.29 | |

Figure 5:
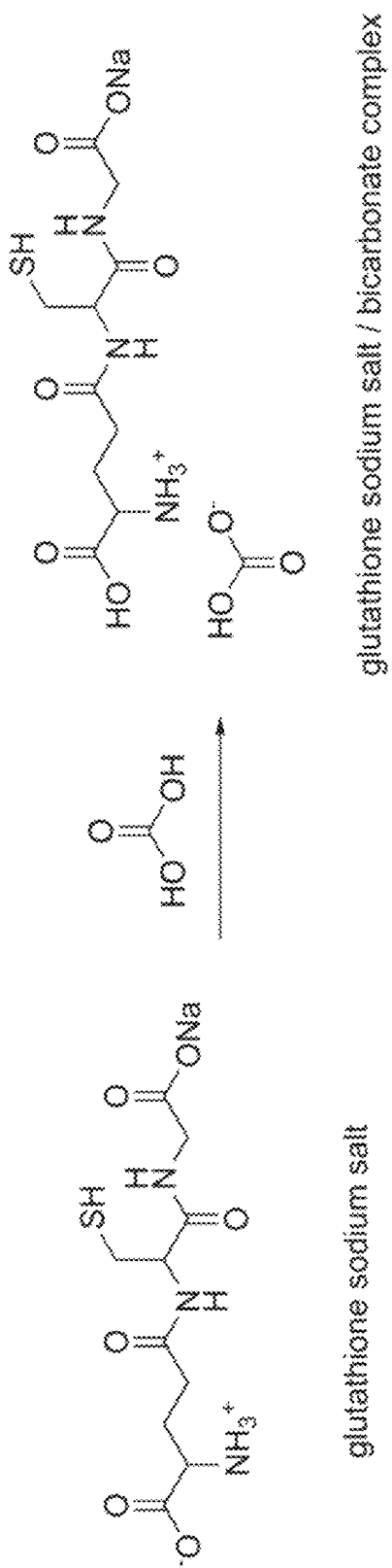
FIG. 5 is a reaction scheme depicting the reaction between glutathione sodium salt and carbonic acid to form a glutathione sodium salt/bicarbonate complex.

This corresponds to a carbonic acid content of 18.2 g/L (0.29 moles), or about 30% of a molar equivalent to the two APIs combined. Given that the solubility of $CO_2$ in water under 1 atmosphere of $CO_2$ at 0° C. is 0.034 g/L, it may be inferred that the solutes present help stabilize carbonic acid in an unexpected manner. The L-glutathione reduced sodium salt is most likely responsible for this stabilization, as it is capable of forming a carbonic acid complex, as shown in FIG. 5.

Having now fully described the compounds, compositions, methods, preparations, and products herein, it will be understood by those of skill in the art that the same can be performed within a wide and equivalent range of conditions, formulations, and other parameters without affecting the scope of the compounds, compositions, methods, preparations, and products provided herein or any embodiment thereof. All patents, patent applications, and publications cited herein are fully incorporated by reference herein in their entirety.

What is claimed is:

1. A preparation comprising an aqueous solution in a closed container with a headspace, wherein:
   (i) the aqueous solution comprises a salt having Formula I:

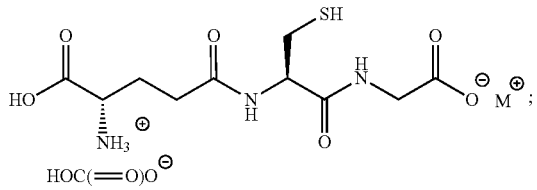

(ii) the atmosphere of the headspace comprises 90% or more carbon dioxide by volume; and
   (iii) $M^+$ is $Na^+$, $Li^+$, $K^+$ or $Cs^+$.

2. The preparation of claim 1, wherein the aqueous solution has a pH of 6.0±0.4 for 24 hours or more at about 5° C.

3. The preparation of claim 2, wherein the aqueous solution has a pH of 6.0±0.1 for 24 hours or more at about 5° C.

4. The preparation of claim 1, wherein the aqueous solution further comprises a salt having Formula II:

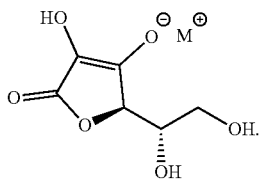

wherein $M^+$ is $Na^+$, $Li^+$, $K^+$ or $Cs^+$.

5. The preparation of claim 1, wherein the aqueous solution further comprises a salt having Formula III:

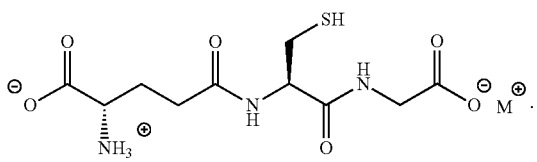

wherein $M^+$ is $Na^+$, $Li^+$, $K^+$ or $Cs^+$.

6. The preparation of claim 1, wherein the atmosphere of the headspace comprises 95% or more of carbon dioxide by volume.

7. The preparation of claim 1, wherein the aqueous solution comprises about 10 wt % to about 20 wt % of the salt having Formula I.

8. The preparation of claim 7, wherein the aqueous solution comprises about 13 wt % to about 17 wt % of the salt having Formula I.

9. The preparation of claim 8, wherein the aqueous solution comprises about 14.7 wt % of the salt having Formula I.

10. The preparation of claim 4, wherein the aqueous solution comprises about 5 wt % to about 15 wt % of the salt having Formula II.

11. The preparation of claim 10, wherein the aqueous solution comprises about 7 wt % to about 11 wt % of the salt having Formula II.

12. The preparation of claim 11, wherein the aqueous solution comprises about 9.1 wt % of the salt having Formula II.

13. The preparation of claim 1, wherein the aqueous solution has a density of about 1.13 g/L.

14. The preparation of claim 1, wherein the aqueous solution is frozen.

15. The preparation of claim 1, wherein $M^+$ is $Na^+$.

16. The preparation of claim 1, packaged as a single unit dose.

17. The preparation of claim 1, wherein the preparation is a pharmaceutical product.

* * * * *